(12) United States Patent
Lin et al.

(10) Patent No.: US 10,577,366 B2
(45) Date of Patent: Mar. 3, 2020

(54) CRYSTALLINE FORMS OF A COMPOUND THAT INHIBITS BROMODOMAIN

(71) Applicant: Plexxikon Inc., Berkeley, CA (US)

(72) Inventors: Jack Lin, Hercules, CA (US); Marika Nespi, Berkeley, CA (US); Jason Walters, Union City, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 15/925,270

(22) Filed: Mar. 19, 2018

(65) Prior Publication Data

US 2018/0265508 A1    Sep. 20, 2018

Related U.S. Application Data

(60) Provisional application No. 62/473,903, filed on Mar. 20, 2017.

(51) Int. Cl.
| | |
|---|---|
| *C07D 471/04* | (2006.01) |
| *A61K 31/437* | (2006.01) |
| *A61K 45/06* | (2006.01) |

(52) U.S. Cl.
CPC .......... *C07D 471/04* (2013.01); *A61K 31/437* (2013.01); *A61K 45/06* (2013.01)

(58) Field of Classification Search
CPC ..... C07D 471/04; A61K 31/437; A61K 45/06
USPC ........................................................ 514/300
See application file for complete search history.

(56) References Cited

U.S. PATENT DOCUMENTS

| | | |
|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West et al. |
| 7,531,568 B2 | 5/2009 | Lin et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,759,475 B2 | 7/2010 | West |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |

(Continued)

FOREIGN PATENT DOCUMENTS

| | | |
|---|---|---|
| WO | WO 2007/013896 | 2/2007 |
| WO | WO 2010/111527 | 9/2010 |

(Continued)

OTHER PUBLICATIONS

Marco Magistri et al , The BET-Bromodomain Inhibitor reduces inflammation . (Year: 2016).*
Wenxian Fu et al. Epigenetic Modulation of Type-1 diabetes . . . (Year: 2014).*
ICH Harmonised Triperte Guidelines . . . ICH commitee (Year: 1999).*

(Continued)

*Primary Examiner* — Rita J Desai
(74) *Attorney, Agent, or Firm* — Sheppard Mullin Richter & Hampton LLP

(57) ABSTRACT

Forms of 4-(1-(1,1-di(pyridin-2-yl)ethyl)-6-(3,5-dimethyl-isoxazol-4-yl)-1H-pyrrolo[3,2-b]pyridin-3-yl)benzoic acid were prepared and characterized in the solid state:

Compound I

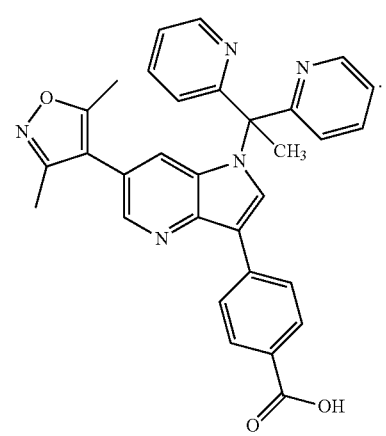

Also provided are processes of manufacture and methods of using the forms of Compound I.

16 Claims, 15 Drawing Sheets

(56) References Cited

U.S. PATENT DOCUMENTS

| | | | |
|---|---|---|---|
| 8,865,735 B2 | 10/2014 | Diodone et al. | |
| 8,901,118 B2 | 12/2014 | Zhang et al. | |
| 8,901,301 B2 | 12/2014 | Ibrahim et al. | |
| 8,912,204 B2 | 12/2014 | Ibrahim et al. | |
| 9,096,593 B2 | 8/2015 | Zhang et al. | |
| 9,150,570 B2 | 10/2015 | Ibrahim et al. | |
| 9,169,250 B2 | 10/2015 | Zhang et al. | |
| 9,260,437 B2 | 2/2016 | Ibrahim et al. | |
| 9,358,235 B2 | 6/2016 | Bollag et al. | |
| 9,440,969 B2 | 9/2016 | Ibrahim et al. | |
| 9,447,089 B2 | 9/2016 | Desai et al. | |
| 9,469,640 B2 | 10/2016 | Wu et al. | |
| 9,487,515 B2 | 11/2016 | Zhang et al. | |
| 9,550,768 B2 | 1/2017 | Zhang et al. | |
| 9,617,267 B2 | 4/2017 | Ibrahim et al. | |
| 9,624,213 B2 | 4/2017 | Ibrahim et al. | |
| 9,663,517 B2 | 5/2017 | Desai et al. | |
| 9,676,748 B2 | 6/2017 | Wu et al. | |
| 9,682,981 B2 | 6/2017 | Zhang et al. | |
| 9,695,169 B2 | 7/2017 | Ibrahim | |
| 9,718,847 B2 | 8/2017 | Zhang et al. | |
| 9,730,918 B2 | 8/2017 | Bollag et al. | |
| 9,745,298 B2 | 8/2017 | Ibrahim et al. | |
| 9,771,363 B2 * | 9/2017 | Ibrahim | C07D 471/04 |
| 9,771,369 B2 | 9/2017 | Lin et al. | |
| 9,776,998 B2 | 10/2017 | Ibrahim et al. | |
| 9,802,932 B2 | 10/2017 | Ibrahim et al. | |
| 9,814,714 B2 | 11/2017 | Ibrahim et al. | |
| 9,822,109 B2 | 11/2017 | Zhang et al. | |
| 9,844,539 B2 | 12/2017 | Wu et al. | |
| 9,856,259 B2 | 1/2018 | Shi et al. | |
| 9,873,700 B2 | 1/2018 | Zhang et al. | |
| 9,975,894 B2 * | 5/2018 | Ibrahim | C07D 471/04 |
| 2004/0142864 A1 | 7/2004 | Bremer et al. | |
| 2004/0171062 A1 | 9/2004 | Hirth et al. | |
| 2005/0048573 A1 | 3/2005 | Artis et al. | |
| 2005/0079548 A1 | 4/2005 | Artis et al. | |
| 2005/0164300 A1 | 7/2005 | Artis et al. | |
| 2005/0170431 A1 | 8/2005 | Ibrahim et al. | |
| 2006/0058339 A1 | 3/2006 | Ibrahim et al. | |
| 2006/0135540 A1 | 6/2006 | Lin et al. | |
| 2006/0160135 A1 | 7/2006 | Wang et al. | |
| 2007/0066641 A1 | 3/2007 | Ibrahim et al. | |
| 2007/0072904 A1 | 3/2007 | Lin et al. | |
| 2008/0221127 A1 | 9/2008 | Lin et al. | |
| 2008/0234349 A1 | 9/2008 | Lin et al. | |
| 2008/0249137 A1 | 10/2008 | Lin et al. | |
| 2010/0190777 A1 | 7/2010 | Wu et al. | |
| 2011/0092538 A1 | 4/2011 | Spevak et al. | |
| 2011/0112127 A1 | 5/2011 | Zhang et al. | |
| 2011/0166174 A1 | 7/2011 | Ibrahim et al. | |
| 2011/0183988 A1 | 7/2011 | Ibrahim et al. | |
| 2012/0015966 A1 | 1/2012 | Lin et al. | |
| 2012/0053177 A1 | 3/2012 | Ibrahim et al. | |
| 2012/0122860 A1 | 5/2012 | Visor et al. | |
| 2012/0165366 A1 | 6/2012 | Ibrahim et al. | |
| 2012/0245174 A1 | 9/2012 | Ibrahim et al. | |
| 2013/0237531 A1 | 9/2013 | Wu et al. | |
| 2013/0261117 A1 | 10/2013 | Ibrahim et al. | |
| 2013/0303534 A1 | 11/2013 | Ibrahim et al. | |
| 2014/0038948 A1 | 2/2014 | Wu et al. | |
| 2014/0128390 A1 | 5/2014 | Lin et al. | |
| 2014/0303121 A1 | 10/2014 | Zhang et al. | |
| 2014/0303187 A1 | 10/2014 | Wu et al. | |
| 2015/0290205 A1 | 10/2015 | Ibrahim et al. | |
| 2016/0176865 A1 | 6/2016 | Ibrahim et al. | |
| 2016/0326162 A1 | 11/2016 | Lin et al. | |
| 2016/0340357 A1 | 11/2016 | Ibrahim et al. | |
| 2017/0029413 A1 | 2/2017 | Holladay et al. | |
| 2017/0081326 A1 * | 3/2017 | Ibrahim | C07D 471/04 |
| 2017/0157120 A1 | 6/2017 | Ibrahim et al. | |
| 2017/0158690 A1 | 6/2017 | Wu et al. | |
| 2017/0247370 A1 | 8/2017 | Zhang et al. | |
| 2017/0267660 A1 | 9/2017 | Lin et al. | |
| 2017/0283423 A1 | 10/2017 | Zhang et al. | |
| 2017/0319559 A1 | 11/2017 | Wu et al. | |
| 2017/0320899 A1 | 11/2017 | Zhang et al. | |
| 2017/0334909 A1 | 11/2017 | Ibrahim et al. | |
| 2017/0349572 A1 | 12/2017 | Wu et al. | |
| 2017/0362231 A1 | 12/2017 | Ibrahim et al. | |
| 2018/0002332 A1 | 1/2018 | Ibrahim et al. | |
| 2018/0030051 A1 | 2/2018 | Ibrahim et al. | |
| 2018/0055828 A1 | 3/2018 | Bollag | |
| 2018/0072722 A1 | 3/2018 | Zhang et al. | |
| 2018/0099939 A1 | 4/2018 | Zhang et al. | |
| 2018/0099975 A1 | 4/2018 | Zhang et al. | |
| 2018/0111929 A1 | 4/2018 | Ibrahim | |
| 2018/0111930 A1 | 4/2018 | Desai | |
| 2018/0215763 A1 | 8/2018 | Wu et al. | |
| 2018/0305358 A1 | 10/2018 | Ibrahim et al. | |
| 2018/0327403 A1 | 11/2018 | Ibrahim et al. | |
| 2019/0119273 A1 | 4/2019 | Ibrahim et al. | |

FOREIGN PATENT DOCUMENTS

| | | |
|---|---|---|
| WO | WO 2010/129467 | 11/2010 |
| WO | WO 2014/145051 | 9/2014 |
| WO | WO 2017/053243 | 3/2017 |

OTHER PUBLICATIONS

U.S. Appl. No. 16/001,534, filed Jun. 6, 2018, Zhang et al.
U.S. Appl. No. 16/043,821, filed Jul. 24, 2018, Ibrahim et al.
U.S. Appl. No. 16/058,945, filed Aug. 8, 2018, Wu.
U.S. Appl. No. 16/109,199, filed Aug. 22, 2018, Wu.
U.S. Appl. No. 16/123,612, filed Sep. 6, 2018, Desai et al.
U.S. Appl. No. 16/148,244, filed Oct. 1, 2018, Zhang et al.
U.S. Appl. No. 16/158,107, filed Oct. 11, 2018, Ibrahim et al.
U.S. Appl. No. 16/172,573, filed Oct. 26, 2018, Rezaei et al.
Andres, "Polymorphs in Pharmaceutical products," presented at 23rd Annual Pharmaceutical/Chemical Patent Practice Update, Dec. 9, 2009, available for download at: https://www.njipla.org/event-831656. 38 pages.
Bucar, et al. Disappearing polymorphs revisited. Angew Chem Int Ed Engl. Jun. 8, 2015;54(24):6972-93.
Cheung, et al. BET N-terminal bromodomain inhibition selectively blocks Th17 cell differentiation and ameliorates colitis in mice. Proc Natl Acad Sci U S A. Mar. 14, 2017;114(11):2952-2957. doi: 10.1073/pnas.1615601114. Epub Mar. 6, 2017.
International Search Report and Written Opinion dated May 28, 2018 for PCT/US2018/023127. 12 pages.
Kharenko, et al. RVX-297—a novel BD2 selective inhibitor of BET bromodomains. Biochem Biophys Res Commun. Aug. 12, 2016;477(1):62-7. doi: 10.1016/j.bbrc.2016.06.021. Epub Jun. 6, 2016.
Lee, et a. Nonselective inhibition of the epigenetic transcriptional regulator BET induces marked lymphoid and hematopoietic toxicity in mice. Toxicol Appl Pharmacol. Jun. 1, 2016;300:47-54. doi: 10.1016/j.taap.2016.03.013. Epub Apr. 11, 2016.
Papavassiliou, et al. Bromodomains: pockets with therapeutic potential. Trends Mol Med. Sep. 2014;20(9):477-8. doi: 10.1016/j.molmed.2014.06.004. Epub Jun. 28, 2014.
Park-Min, et al. Inhibition of osteoclastogenesis and inflammatory bone resorption by targeting BET proteins and epigenetic regulation. Nat Commun. Nov. 13, 2014;5:5418. doi: 10.1038/ncomms6418.
U.S. Appl. No. 16/358,608, filed Mar. 19, 2019, Zhang et al.
U.S. Appl. No. 16/400,801, filed May 1, 2019, Ibrahim et al.
U.S. Appl. No. 16/441,610, filed Jun. 14, 2019, Ibrahim et al.
U.S. Appl. No. 16/510,617, filed Jul. 12, 2019, Ibrahim et al.
U.S. Appl. No. 16/510,764, filed Jul. 12, 2019, Ibrahim et al.
U.S. Appl. No. 16/510,757, filed Jul. 12, 2019, Ibrahim et al.
Bauer, et al. Polymorphism—A Critical Consideration in Pharmaceutical Development, Manufacturing, and Stability. Journal of Validation Technology. 2008; 15-23.

* cited by examiner

CRYSTALLINE FORMS OF A COMPOUND THAT INHIBITS BROMODOMAIN

CROSS-REFERENCE TO RELATED APPLICATIONS

This application claims the benefit under 35 U.S.C. § 119(e) of U.S. Provisional Application 62/473,903, filed Mar. 20, 2017, of which is hereby incorporated by reference in its entirety.

FIELD

The present disclosure relates generally to solid forms of compounds that modulate or inhibit the activity of bromodomain proteins, pharmaceutical compositions thereof, therapeutic uses thereof, and processes for making the solid forms.

BACKGROUND

There remains a need to develop effective treatments for subjects suffering from or at risk of protein kinase mediated disease or condition. Suitable compounds, including Compound I, for the treatment of such diseases and conditions are disclosed in U.S. Patent Publication No. 2017-0081326, the disclosure of which is hereby incorporated by reference in its entirety.

There also remains a need for high purity solid forms of Compound I that are efficacious for the treatment of diseases modulated by bromodomain proteins.

SUMMARY

The present disclosure provides solid forms of Compound I of the formula:

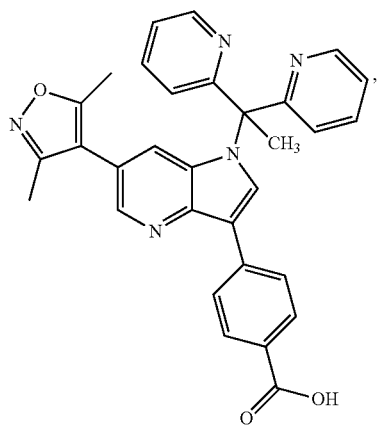

Compound I and salts, co-crystals, solvates, and hydrates thereof. Also described herein are processes for making the forms of Compound I, pharmaceutical compositions comprising solid forms of Compound I, and methods for using such forms and pharmaceutical compositions in the treatment of diseases mediated by bromodomain proteins.

DETAILED DESCRIPTION

Figure 1:
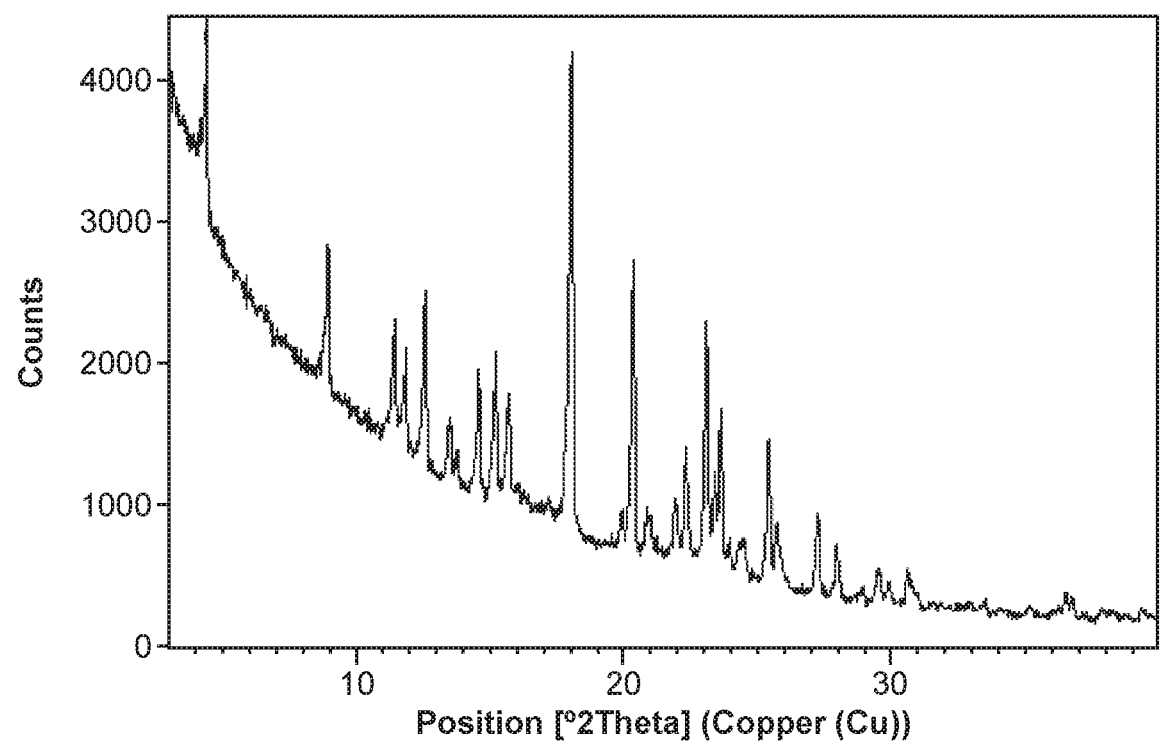
FIG. 1 is an X-ray powder diffractogram of Compound I Form A.

The compound 4-(1-(1,1-di(pyridin-2-yl)ethyl)-6-(3,5-dimethylisoxazol-4-yl)-1H-pyrrolo[3,2-b]pyridin-3-yl)benzoic acid, designated herein as Compound I or Compound I (free acid), has the following formula:

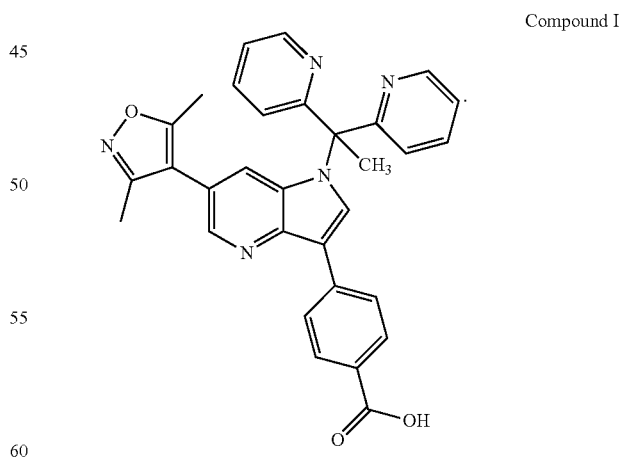

Compound I

Compound I is an inhibitor or modulator of bromodomain proteins. The synthesis and method of use thereof is described in U.S. Patent Publication No. 2017-0081326, which is herein incorporated by reference in its entirety.

The present disclosure relates to various solid forms of Compound I, and processes for making such solid forms.

Additional solid forms of Compound I are also described herein, as well as the processes of making such forms. For instance, in some embodiments, solid forms of Compound I may include salts, co-crystals, solvates, or hydrates of Compound I. In some embodiments, solid forms of Compound I may include an amorphous form of Compound I.

1. Definitions

As used in the present specification, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±2.5%. In certain other embodiments, the term "about" includes the indicated amount±1%. Also, to the term "about X" includes description of "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

Forms of Compound I or salts, co-crystals, solvates, or hydrates thereof are provided herein. In one embodiment, reference to a form of Compound I or a salt, co-crystal, solvate, or hydrate thereof means that at least 50% to 99% (e.g., at least 50%, at least 55%, at least 60%, at least 65%, at least 70%, at least 75%, at least 80%, at least 85%, at least 90%, at least 95%, or at least 99%) of Compound I or a salt, co-crystal, solvate, or hydrate thereof present in a composition is in the designated form. For instance, in one embodiment, reference to Compound I Form A means that at least 50%, at least 55%, at least 60%, at least 65%, at least 70%, at least 75%, at least 80%, at least 85%, at least 90%, at least 95%, or at least 99% of Compound I present in a composition is in Form A.

The term "solid form" refers to a type of solid-state material that includes amorphous as well as crystalline forms. The term "crystalline form" refers to polymorphs as well as solvates, hydrates, etc. The term "polymorph" refers to a particular crystal structure having particular physical properties such as X-ray diffraction, melting point, and the like.

The term "co-crystal" refers to a molecular complex of a compound disclosed herein and one or more non-ionized co-crystal formers connected via non-covalent interactions. In some embodiments, the co-crystals disclosed herein may include a non-ionized form of Compound I (e.g., Compound I free acid) and one or more non-ionized co-crystal formers, where non-ionized Compound I and the co-crystal former(s) are connected through non-covalent interactions. In some embodiments, co-crystals disclosed herein may include an ionized form of Compound I (e.g., a salt of Compound I) and one or more non-ionized co-crystals formers, where ionized Compound I and the co-crystal former(s) are connected through non-covalent interactions. Co-crystals may additionally be present in anhydrous, solvated or hydrated forms. In certain instances, co-crystals may have improved properties as compared to the parent form (i.e., the free molecule, zwitterion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

The term "co-crystal former" or "co-former" refers to one or more pharmaceutically acceptable bases or pharmaceutically acceptable acids disclosed herein in association with Compound I, or any other compound disclosed herein.

The term "solvate" refers to a complex formed by combination of solvent molecules with molecules or ions of the solute. The solvent can be an organic compound, an inorganic compound, or a mixture of both. As used herein, the term "solvate" includes a "hydrate" (i.e., a complex formed by combination of water molecules with molecules or ions of the solute), hemi-hydrate, channel hydrate, etc. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

Any formula or structure given herein, including Compound I, is also intended to represent unlabeled forms as well as isotopically labeled forms of the compounds. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$, nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}$F, $^{18}$F, $^{19}$F; chloro includes for example $^{35}$Cl, $^{36}$Cl, $^{37}$Cl, $^{38}$Cl, $^{39}$Cl; and the like.

As used herein, the terms "treat," "treating," "therapy," "therapies," and like terms refer to the administration of material, e.g., any one or more solid, crystalline or polymorphs of Compound I as described herein in an amount effective to prevent, alleviate, or ameliorate one or more symptoms of a disease or condition, i.e., indication, and/or to prolong the survival of the subject being treated.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration (IC$_{50}$) or excitation concentration (EC$_{50}$) of the compound for an inhibitor or activator, respectively, with respect to, for example, an enzyme.

As used herein, the term "protein kinase mediated disease or condition," refers to a disease or condition in which the biological function of a protein kinase, including any mutations thereof, affects the development, course, and/or symptoms of the disease or condition, and/or in which modulation of the protein kinase alters the development, course, and/or symptoms of the disease or condition. The protein kinase mediated disease or condition includes a disease or condition for which inhibition provides a therapeutic benefit, e.g. wherein treatment with protein kinase inhibitor(s), including one or more solid, crystalline or polymorphs of Compound I or as described herein, provides a therapeutic benefit to the subject suffering from or at risk of the disease or condition.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" or "patient" refers to a living organism that is treated with compounds as described herein, including, but not limited to, any mammal, such as a human, other primates, sports animals, animals of commercial interest such as cattle, farm animals such as horses, or pets such as dogs and cats.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

In some embodiments, the phrase "substantially shown in Figure" as applied to an X-ray powder diffractogram is meant to include a variation of ±0.2 °2θ or ±0.1 °2θ, as applied to DSC thermograms is meant to include a variation of ±3° Celsius, and as applied to thermogravimetric analysis (TGA) is meant to include a variation of ±2% in weight loss.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In addition, abbreviations as used herein have respective meanings as follows:

| | |
|---|---|
| 2-MeTHF | 2-methyltetrahydrofuran |
| ACN | acetonitrile |
| DCM | dichloromethane |
| DMF | dimethylformamide |
| DMSO | dimethylsulfoxide |
| DSC | differential scanning calorimetry |
| DVS | dynamic vapor sorption |
| EtOAc | ethyl acetate |
| EtOH | ethanol |
| IPAc | isopropyl acetate |
| KOt-Bu | potassium tert-butoxide |
| LC/MS | Liquid chromatography mass spectrometry |
| Me | methyl |
| MeOH | methanol |
| MIBK | 4-Methyl-2-pentanone |
| MTBE | methyl tert-butyl ether |
| NIS | N-iodosuccinimide |
| NMR | Nuclear magnetic resonance spectroscopy |
| Ph | phenyl |
| RH | relative humidity |
| RT | room temperature |
| SCXRD | Single Crystal X-ray Diffraction |
| TGA | thermogravimetric analysis |
| THF | tetrahydrofuran |
| v/v | volume to volume |
| w/w | weight to weight |
| XRPD | X-ray powder diffraction |

2. Forms of Compound I

As described generally above, the present disclosure provides crystalline forms of Compound I and salts, co-crystals, solvates, or hydrates thereof. Additional forms (including amorphous forms) are also discussed further herein. It is of note that the crystalline forms of Compound I and salts, co-crystals, solvates, or hydrates thereof, and other forms (e.g., amorphous forms) of Compound I and salts, co-crystals, solvates, or hydrates thereof are collectively referred to herein as "forms of Compound I."

In some embodiments, Compound I is a free acid. In some embodiments, Compound I is a salt or a co-crystal. In some embodiments, Compound I is a pharmaceutically acceptable salt or co-crystal. In some embodiments, Compound I is a solvate. In some embodiments, Compound I is a hydrate. In some embodiments, Compound I is an anhydrate.

In some embodiments, Compound I is an amorphous form.

Compound I Form A

The present disclosure provides, in one embodiment, a crystalline form 4-(1-(1,1-di(pyridin-2-yl)ethyl)-6-(3,5-dimethylisoxazol-4-yl)-1H-pyrrolo[3,2-b]pyridin-3-yl)benzoic acid ("Compound I Form A" or "Form A") characterized by an X-ray powder diffractogram comprising the following peaks: 14.6, 18.1, and 20.4 °2θ±0.2 °2θ, as determined on a diffractometer using Cu-Kα radiation. In one embodiment, the diffractogram of Compound I Form A further comprises one or more peaks at: 11.9, 23.1, or 25.4 °2θ±0.2 °2θ. In one embodiment, Compound I Form A is characterized by the X-ray powder diffractogram as substantially shown in FIG. 1.

Figure 2:
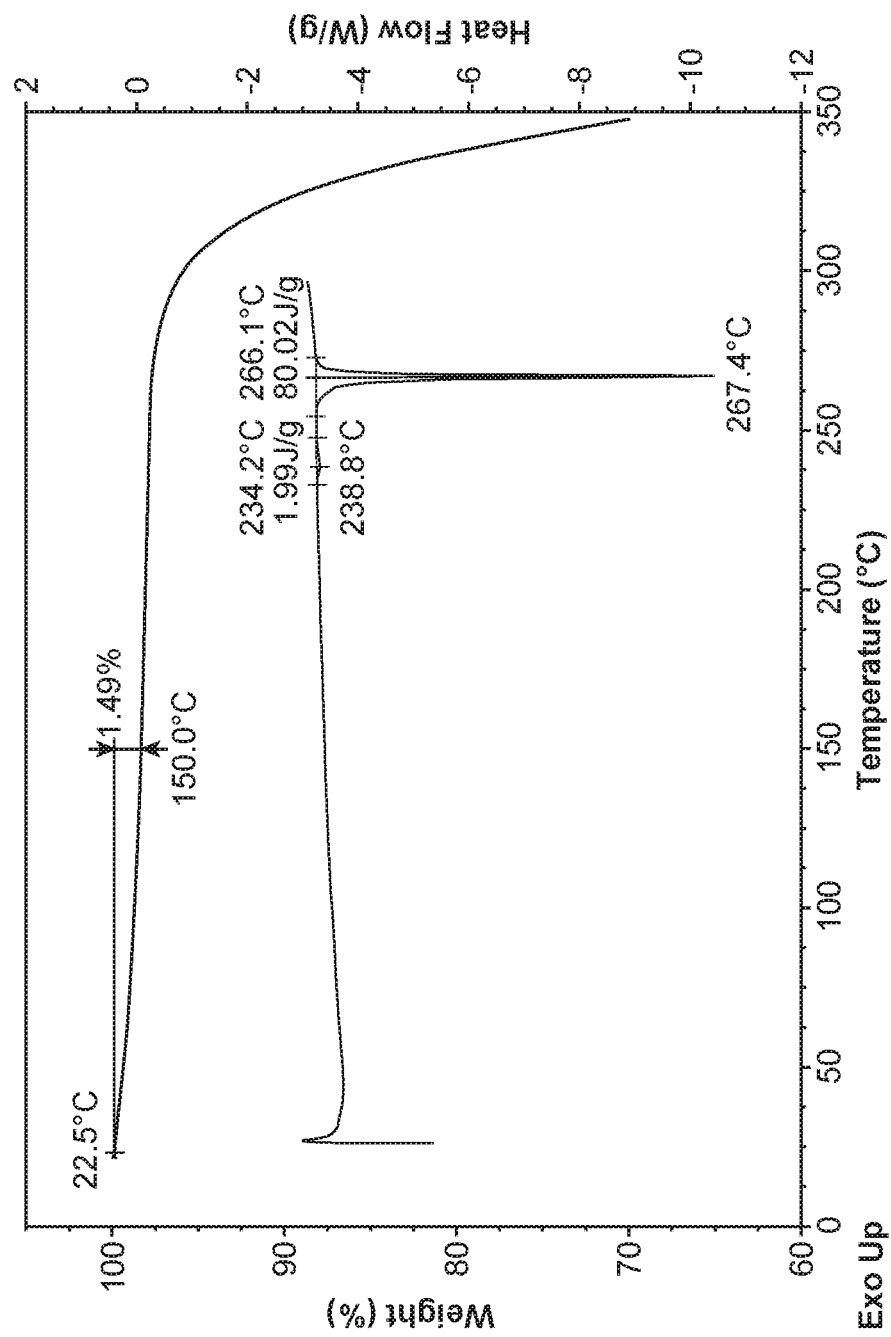
FIG. 2 is a thermogravimetric analysis (TGA) (top line) and a differential scanning calorimeter (DSC) curve (bottom line) of Compound I Form A.

In one embodiment, Compound I Form A is characterized by a differential scanning calorimetry (DSC) curve that comprises an endotherm at about 266° C. (onset temperature). In one embodiment, the DSC curve of Compound I Form A comprises an additional endotherm at about 234° C. (onset temperature). In one embodiment, Compound I Form A is characterized by the DSC curve as substantially shown in FIG. 2 (bottom line).

In one embodiment, Compound I Form A is characterized by a thermogravimetric analysis (TGA) thermogram showing a weight loss of about 1.5% up to about 150° C. In one embodiment, Compound I Form A is characterized by the thermogram as substantially shown in FIG. 2 (top line).

Some embodiments provide for Compound I Form A having unit cell parameters: a=19.3990(10) Å, b=8.2109(4) Å, and c=16.1667(8) Å. Some embodiments provide for Compound I Form A having unit cell parameters: α=90°, β=94.057(3)°, and γ=90°.

In one embodiment, Compound I Form A has unit cell parameters: a=19.3990(10) Å, b=8.2109(4) Å, c=16.1667(8) Å, α=90°, β=94.057(3)°, and γ=90°.

In one embodiment, Compound I Form A has unit cell parameters: a=19.3990(10) Å, b=8.2109(4) Å, c=16.1667(8) Å, α=90°, β=94.057(3)°, γ=90°, and volume=2568.6(2) Å$^3$.

In one embodiment, a single crystal of Compound I Form A is in a monoclinic crystal system and P2√c space group. In one embodiment, Compound I Form A is characterized by one or more of the crystal structure parameters of Table 11.

Compound I Form B

The present disclosure provides, in one embodiment, a crystalline form 4-(1-(1,1-di(pyridin-2-yl)ethyl)-6-(3,5-dimethylisoxazol-4-yl)-1H-pyrrolo[3,2-b]pyridin-3-yl)benzoic acid ("Compound I Form B" or "Form B") characterized by an X-ray powder diffractogram comprising the following peaks: 19.0, 21.0, and 24.8 °2θ±0.2 °2θ, as determined on a diffractometer using Cu-Kα radiation. In one embodiment, the diffractogram of Compound I Form B further comprises one or more peaks at: 10.9, 17.2, or 18.0 °2θ±0.2 °2θ. In one embodiment, Compound I Form B is characterized by the X-ray powder diffractogram as substantially shown in FIG. 4.

In one embodiment, Compound I Form B is characterized by a differential scanning calorimetry (DSC) curve that comprises endotherms at about 74° C., about 234° C. and about 267° C. (onset temperature). In one embodiment, Compound I Form B is characterized by the DSC curve as substantially shown in FIG. 5 (bottom line).

In one embodiment, Compound I Form B is characterized by a thermogravimetric analysis (TGA) thermogram showing a weight loss of about 8.2% up to about 150° C. In one embodiment, Compound I Form B is characterized by the thermogram as substantially shown in FIG. 5 (top line).

Compound I Form C

The present disclosure provides, in one embodiment, a crystalline form 4-(1-(1,1-di(pyridin-2-yl)ethyl)-6-(3,5-dimethylisoxazol-4-yl)-1H-pyrrolo[3,2-b]pyridin-3-yl)benzoic acid ("Compound I Form C" or "Form C") characterized by an X-ray powder diffractogram comprising the following peaks: 8.8, 17.1, and 17.7 °2θ±0.2 °2θ, as determined on a diffractometer using Cu-Kα radiation. In one embodiment, the diffractogram of Compound I Form C further comprises one or more peaks at: 11.6 or 15.1 °2θ±0.2 °2θ. In one embodiment, Compound I Form C is characterized by the X-ray powder diffractogram as substantially shown in FIG. 7.

In one embodiment, Compound I Form C is characterized by a differential scanning calorimetry (DSC) curve that comprises endotherms at about 232° C. and about 267° C. (onset temperature). In one embodiment, Compound I Form C is characterized by the DSC curve as substantially shown in FIG. 8 (bottom line).

In one embodiment, Compound I Form C is characterized by a thermogravimetric analysis (TGA) thermogram showing a weight loss of about 1.5% up to about 150° C. In one embodiment, Compound I Form C is characterized by the thermogram as substantially shown in FIG. 8 (top line).

Compound I Form D

Figure 10:
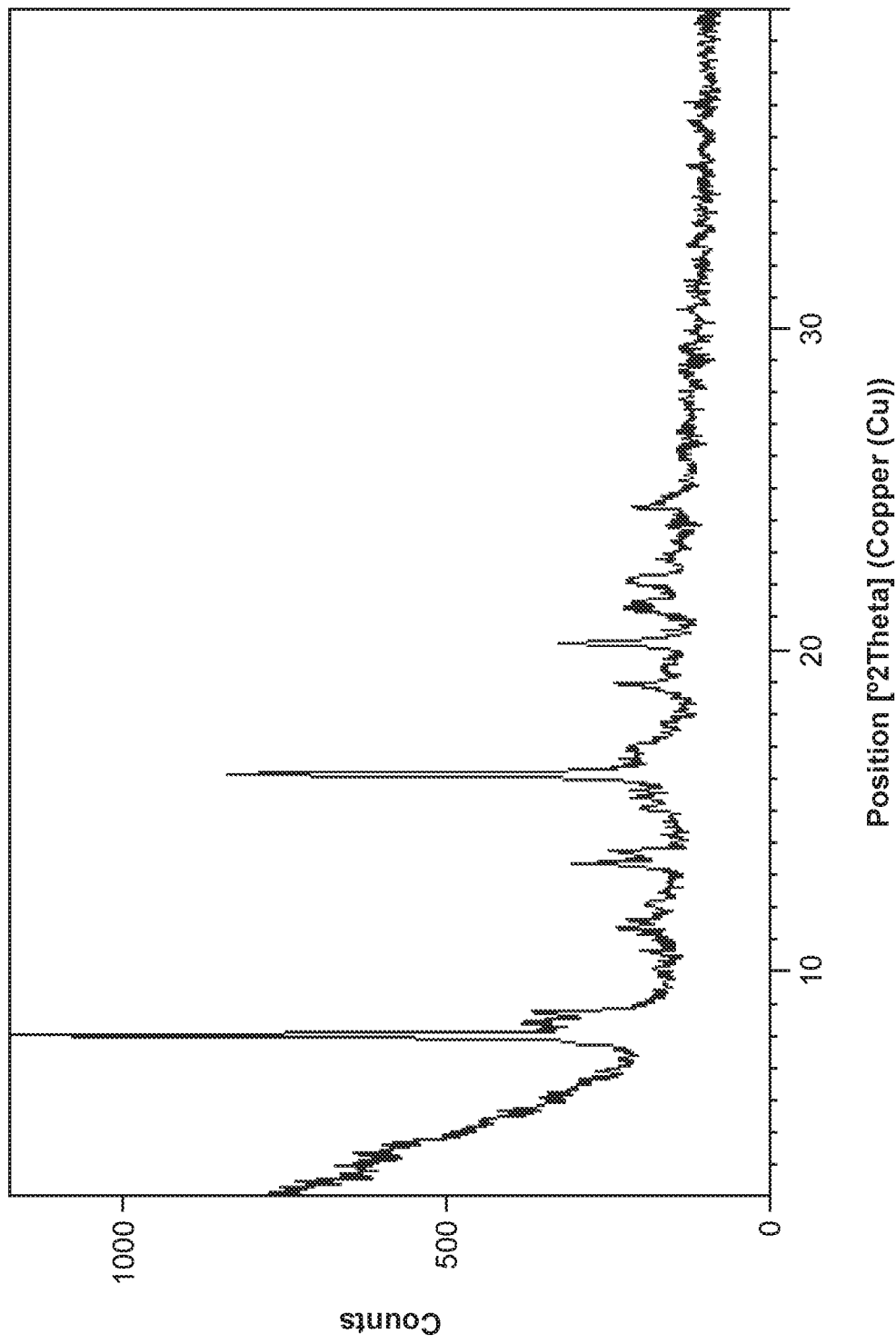
FIG. 10 is an X-ray powder diffractogram of Compound I Form D.

The present disclosure provides, in one embodiment, a crystalline form 4-(1-(1,1-di(pyridin-2-yl)ethyl)-6-(3,5-dimethylisoxazol-4-yl)-1H-pyrrolo[3,2-b]pyridin-3-yl)benzoic acid ("Compound I Form D" or "Form D") characterized by an X-ray powder diffractogram comprising the following peaks: 8.0, 16.1, and 20.2 °2θ±0.2 °2θ, as determined on a diffractometer using Cu-Kα radiation. In one embodiment, the diffractogram of Compound I Form D further comprises one or more peaks at: 13.5 or 22.2 °2θ±0.2 °2θ. In one embodiment, Compound I Form D is characterized by the X-ray powder diffractogram as substantially shown in FIG. 10.

Figure 11:
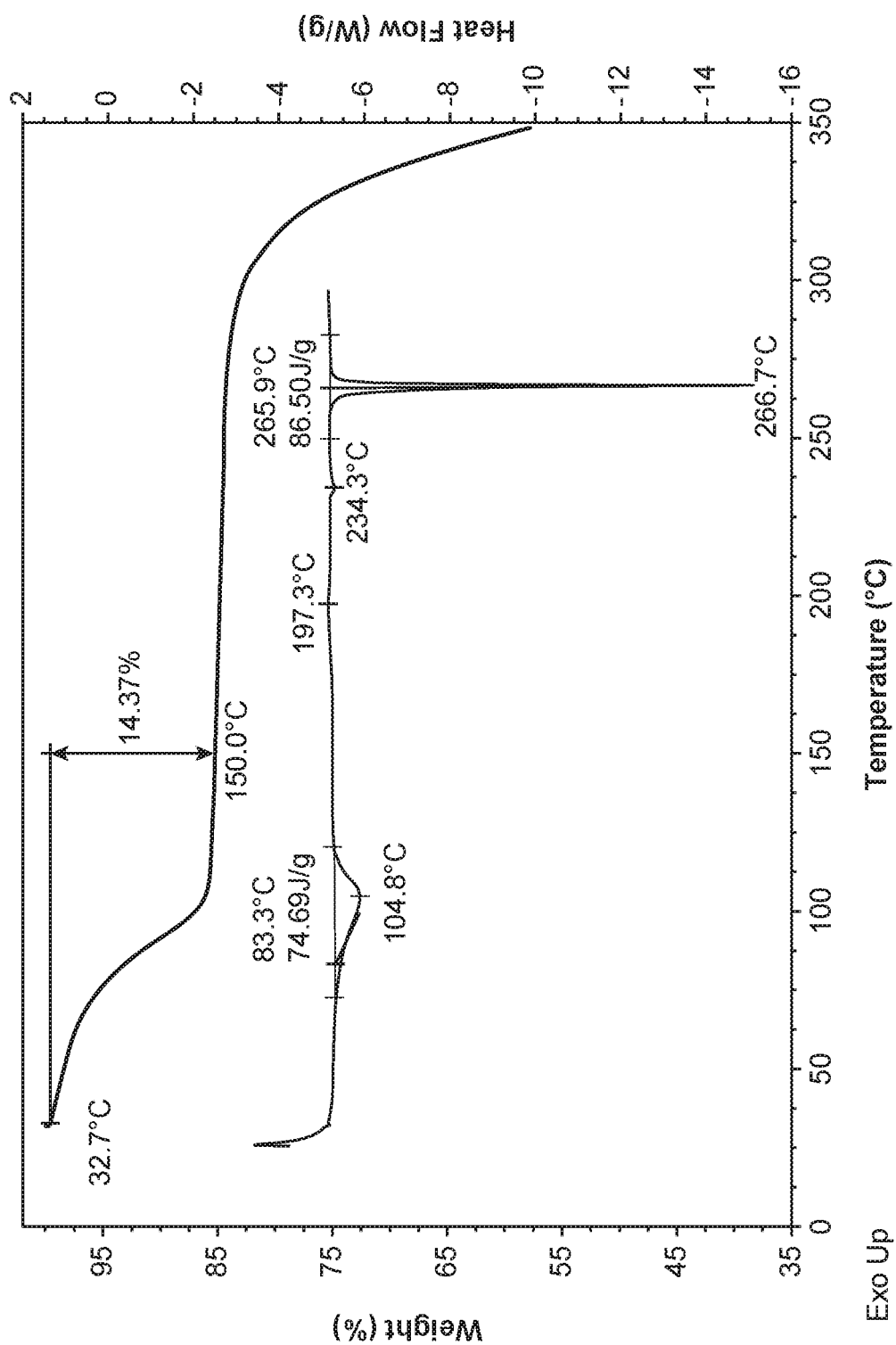
FIG. 11 is a thermogravimetric analysis (TGA) (top line) and a differential scanning calorimeter (DSC) curve (bottom line) of Compound I Form D.

In one embodiment, Compound I Form D is characterized by a differential scanning calorimetry (DSC) curve that comprises endotherms at about 105° C., about 234° C. and about 267° C. (peak temperature). In one embodiment, the DSC curve of Compound I Form D comprises an exotherm at about 197° C. (onset temperature). In one embodiment, Compound I Form D is characterized by the DSC curve as substantially shown in FIG. 11 (bottom line).

In one embodiment, Compound I Form D is characterized by a thermogravimetric analysis (TGA) thermogram showing a weight loss of about 14.4% up to about 150° C. In one embodiment, Compound I Form D is characterized by the thermogram as substantially shown in FIG. 11 (top line).

Compound I Form E

Figure 12:
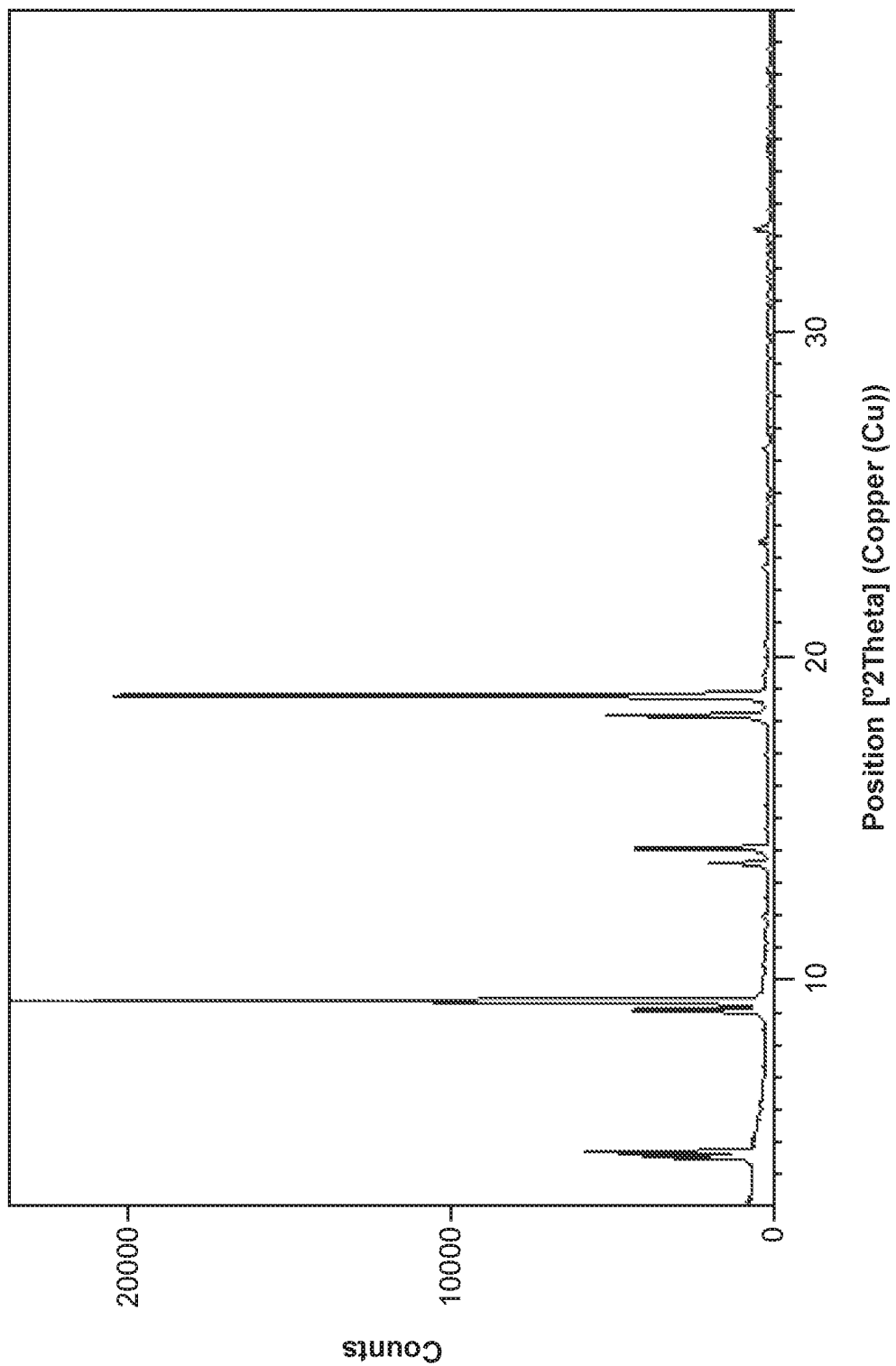
FIG. 12 is an X-ray powder diffractogram of Compound I Form E.

The present disclosure provides, in one embodiment, a crystalline form 4-(1-(1,1-di(pyridin-2-yl)ethyl)-6-(3,5-dimethylisoxazol-4-yl)-1H-pyrrolo[3,2-b]pyridin-3-yl)benzoic acid ("Compound I Form E" or "Form E") characterized by an X-ray powder diffractogram comprising the following peaks: 4.7, 9.4, and 18.8 °2θ±0.2 °2θ, as determined on a diffractometer using Cu-Kα radiation. In one embodiment, the diffractogram of Compound I Form E further comprises one or more peaks at: 9.1, 14.1, or 18.2 °2θ±0.2 °2θ. In one embodiment, Compound I Form E is characterized by the X-ray powder diffractogram as substantially shown in FIG. 12.

In one embodiment, Compound I Form E is characterized by a differential scanning calorimetry (DSC) curve that comprises endotherms at about 131° C., about 229° C., and about 266° C. (onset temperature). In one embodiment, Compound I Form E is characterized by the DSC curve as substantially shown in FIG. 13 (bottom line).

In one embodiment, Compound I Form E is characterized by a thermogravimetric analysis (TGA) thermogram showing a weight loss of about 2.5% up to about 150° C. In one embodiment, Compound I Form E is characterized by the thermogram as substantially shown in FIG. 13 (top line).

3. Pharmaceutical Compositions, Kits, and Modes of Administration

The forms of Compound I as described herein may be administered in a pharmaceutical composition. Thus, provided herein are pharmaceutical compositions comprising one or more of the forms of Compound I described herein and one or more pharmaceutically acceptable vehicles such as carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). The pharmaceutical compositions may be administered alone or in combination with other therapeutic agents.

Some embodiments are directed to pharmaceutical compositions comprising a therapeutically effective amount of a crystalline form of Compound I described herein. In some embodiments, a pharmaceutical composition comprises a crystalline form selected from Compound I Form A, Compound I Form B, Compound I Form C, Compound I Form D, and Compound I Form E; and one or more pharmaceutically acceptable carriers.

Some embodiments are directed to pharmaceutical compositions comprising a crystalline form of Compound I as described herein and one or more pharmaceutically acceptable carriers. In one embodiment, a pharmaceutical composition comprises Compound I, wherein at least 95% of Compound I is in a crystalline form as described herein. In one embodiment, a pharmaceutical composition comprises Compound I, wherein at least 95% of Compound I is in Form A. In one embodiment, a pharmaceutical composition comprises Compound I, wherein at least 95% of Compound I is in Form B. In one embodiment, a pharmaceutical composition comprises Compound I, wherein at least 95% of Compound I is in Form C. In one embodiment, a pharmaceutical composition comprises Compound I, wherein at least 95% of Compound I is in Form D. In one embodiment, a pharmaceutical composition comprises Compound I, wherein at least 95% of Compound I is in Form E.

In one embodiment, a pharmaceutical composition comprises Compound I, wherein at least 97% of Compound I is in a crystalline form as described herein. In one embodiment, a pharmaceutical composition comprises Compound I, wherein at least 97% of Compound I is in Form A. In one embodiment, a pharmaceutical composition comprises Compound I, wherein at least 97% of Compound I is in Form B. In one embodiment, a pharmaceutical composition comprises Compound I, wherein at least 97% of Compound I is in Form C. In one embodiment, a pharmaceutical composition comprises Compound I, wherein at least 97% of Compound I is in Form D. In one embodiment, a pharmaceutical composition comprises Compound I, wherein at least 97% of Compound I is in Form E.

In one embodiment, a pharmaceutical composition comprises Compound I, wherein at least 99% of Compound I is in a crystalline form as described herein. In one embodiment, a pharmaceutical composition comprises Compound I, wherein at least 99% of Compound I is in Form A. In one embodiment, a pharmaceutical composition comprises Compound I, wherein at least 99% of Compound I is in Form B. In one embodiment, a pharmaceutical composition comprises Compound I, wherein at least 99% of Compound I is in Form C. In one embodiment, a pharmaceutical composition comprises Compound I, wherein at least 99% of Compound I is in Form D. In one embodiment, a pharmaceutical composition comprises Compound I, wherein at least 99% of Compound I is in Form E.

In one embodiment, a pharmaceutical composition comprises Compound I, wherein at least 99.5% of Compound I is in a crystalline form as described herein. In one embodiment, a pharmaceutical composition comprises Compound I, wherein at least 99.5% of Compound I is in Form A. In one embodiment, a pharmaceutical composition comprises Compound I, wherein at least 99.5% of Compound I is in Form B. In one embodiment, a pharmaceutical composition comprises Compound I, wherein at least 99.5% of Compound I is in Form C. In one embodiment, a pharmaceutical composition comprises Compound I, wherein at least 99.5% of Compound I is in Form D. In one embodiment, a pharmaceutical composition comprises Compound I, wherein at least 99.5% of Compound I is in Form E.

In one embodiment, a pharmaceutical composition comprises Compound I, wherein at least 99.9% of Compound I is in a crystalline form as described herein. In one embodiment, a pharmaceutical composition comprises Compound I, wherein at least 99.9% of Compound I is in Form A. In one embodiment, a pharmaceutical composition comprises Compound I, wherein at least 99.9% of Compound I is in Form B. In one embodiment, a pharmaceutical composition comprises Compound I, wherein at least 99.9% of Compound I is in Form C. In one embodiment, a pharmaceutical composition comprises Compound I, wherein at least 99.9% of Compound I is in Form D. In one embodiment, a pharmaceutical composition comprises Compound I, wherein at least 99.9% of Compound I is in Form E.

In some embodiments, compositions comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, difatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the present disclosure (as a free-acid, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discreet units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or cod-liver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the compound.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than Cu). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, the compounds as disclosed herein (e.g., one or more solid, crystalline or polymorph forms of Compound I) are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

In another aspect, the present disclosure provides kits or containers that include a Compound I, and any of its forms as described herein, or any of the pharmaceutical compositions thereof described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a bromodomain protein mediated disease or condition; the kit or container disclosed herein may include written instructions for use and/or other indication that the compound or composition is suitable or approved for administration to a mammal, e.g., a human, for a bromodomain-mediated disease or condition; and the compound or composition may be packaged in unit dose or single dose form, e.g., single dose pills, capsules, or the like.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein (e.g., one or more solid, crystalline or polymorph forms of Compound I) may also be used in combination with other therapies, drugs, medical procedures, etc. for treating the same disease. In some embodiments, such combination use includes administration of one or more other therapies, drugs, or medical procedures at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. In some embodiments, use in combination includes use with at least one other therapy, drug or medical procedure that is administered once or infrequently, such as surgery, along with a compound described herein administered within a short time or longer time before or after the other therapy, drug or procedure. In some embodiments, use in combination includes delivery of a compound described herein and one or more other drug therapeutics by the same route or different routes of administration. In some embodiments, a compound described herein and one or more other drug therapeutics may be delivered together in any formulation by the same route of administration, including formulations where the compounds and other drug therapeutic(s) are chemically linked in such a way that they maintain their therapeutic activity when administered. In some embodiments, the other drug therapeutic(s) may be co-administered with a compound described herein. In some embodiments, co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapeutics delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components. In some embodiments, the compounds as disclosed herein may be used in adjuvant or neoadjuvant therapy in combination with other therapies or therapeutic agents as described herein. In some embodiments involving combination use, dosage may be modified for one or more of the compounds of the present disclosure or other therapeutics used in combination, e.g., reduction in the amount dosed relative to a compound or therapy used alone, by methods well known to those of ordinary skill in the art. Exemplary combination therapies are discussed below.

4. Disease Indications and Modulations of Bromodomains

Exemplary Diseases Associated with Bromodomain

Members of the BET (Bromodomain and Extra Terminal) family of bromodomain proteins (BRD2, BRD3, BRD4 and BRDT) have been associated with a variety of disorders including neurological diseases, autoimmune and inflammatory diseases, metabolic diseases (Muller et al. *Expert Rev. Mol. Med.* 2011, September 13; 13:e29; Prinjha et al. *Trends Pharmacol. Sci.* 2012, 33, 146-153; Belkina et al. *J. Immunol.* 2013, 190, 3670-3678; and Belkina et al. *Nature Rev. Cancer* 2012, 12, 465-477) and cancers (Alsarraj et al. *International Journal of Breast Cancer* 2012, 1-7; Barbieri et al. *Briefings in Functional Genomics* 2013, 1-12; Blobel et al. *Cancer Cell* 2011, 20, 287-288; Dang *Cell* 2012, 149, 22-35). In addition, some viruses make use of these proteins to tether their genomes to the host cells chromatin, as part of the process of viral replication (You et al *Cell*, 2004 117, 349-60).

Compound I, and any of its forms as described herein, are useful for treating disorders related to one or more proteins involved in epigenetic regulation, such as proteins containing acetyl-lysine recognition motifs, i.e., bromodomains (e.g., BET proteins, such as BRD2, BRD3, BRD4, and/or BRDT), and e.g., diseases related to abnormal expression of bromodomains, including cell proliferative disorders, cancers, chronic autoimmune, inflammatory conditions, among others.

The presence of bromodomains has been associated with a number of different types of cancers, and other diseases and conditions, as described below. Bromodomain inhibitors such as Compound I, and any of its forms as described herein, are useful in the treatment of systemic or tissue inflammation, inflammatory responses to infection or hypoxia, cellular activation and proliferation, lipid metabolism, fibrosis and in the prevention and treatment of viral infections.

Bromodomain inhibitors such as Compound I, and any of its forms as described herein, are useful in the prevention and treatment of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors such as Compound I, and any of its forms as described herein, are useful in the prevention and treatment of acute inflammatory conditions, including, but not limiting to, such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

Bromodomain inhibitors such as Compound I, and any of its forms as described herein, are useful in the prevention and treatment of: rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes, synovial sarcoma, and acute rejection of transplanted organs.

Bromodomain inhibitors such as Compound I, and any of its forms as described herein, are useful in the prevention and treatment of autoimmune and inflammatory diseases or conditions which involve inflammatory responses to infections with bacteria, viruses, such as herpes virus, human papilloma virus, adenovirus and poxvirus and other DNA viruses; fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors such as Compound I, and any of its forms as described herein, are useful in the prevention and treatment of diseases or conditions associated with ischemia-reperfusion injury, including, but not limiting to, myocardial infarction, cerebro-vascular ischemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors such as Compound I, and any of its forms as described herein, are useful in the prevention and treatment of hypercholesterolemia, atherosclerosis and Alzheimer's disease.

Bromodomain inhibitors such as Compound I, and any of its forms as described herein, are useful in the prevention and treatment of cancers including, but not limiting to, hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

Bromodomain Activity Assays

A number of different assays for bromodomain activity can be utilized for assaying for active modulators and/or determining specificity of a modulator for a particular bromodomain or group. In addition to the assay mentioned in the Examples below, one of ordinary skill in the art will know of other assays that can be utilized and can modify an assay for a particular application.

In certain embodiments, Compound I, and any of its forms as described herein, have an $IC_{50}$ of less than less than 100 nM, less than 50 nM, less than 20 nM, less than 10 nM, less than 5 nM, or less than 1 nM as determined in a generally accepted bromodomain activity assay or a bromodomain activity assay as described herein. In some embodiments, the assay for measuring bromodomain activity includes an assay (e.g., biochemical or cell-bases assays) such as described in U.S. Patent Publication No. 2017-0081326, or an assay known in the art.

Modulation of Bromodomain

In another aspect, the present disclosure provides a method for modulating or inhibiting a bromodomain protein. The method includes administering to a subject an effective amount of Compound I, and any of its forms as described herein, or a composition comprising a compound Compound I, or any of its forms as described herein, thereby, modulating or inhibiting the bromodomain. In some embodiments, the method includes contacting a cell in vivo or in vitro with Compound I, and any of its forms as described herein, or a composition comprising Compound I, and any of its forms as described herein, as described herein.

5. Methods for Treating Conditions Mediated by Bromodomain

In another aspect, the present disclosure provides a method for treating a subject suffering from or at risk of a bromodomain mediated diseases or conditions, wherein inhibition of bromodomain plays a role or provides a benefit. The method includes administering to the subject an effective amount of a Compound I, and any of its forms as described herein, or a composition comprising Compound I, and any of its forms as described herein, as described herein. In certain embodiments, the method involves administering to the subject an effective amount of Compound I, and any of its forms as described herein, as described herein in combination with one or more other therapies or therapeutic agents for the disease or condition. In some embodiments, the method involves administering to the subject an effective amount of Compound I, and any of its forms as described herein, in combination with one or more other therapeutic agents for the disease or condition.

In some embodiments, the present disclosure provides a method of suppressing undesired proliferation of tumor cells mediated by bromodomain. The method includes contacting tumor cells with an effective amount of a Compound I, and any of its forms as described herein. In some instances, the tumor cells are mediated by BET protein, BRD4 protein or a mutant thereof.

In certain embodiments, the present disclosure provides a method of treating a patient, where inhibition of bromodomain (e.g., BET protein or BRD4 protein) provides a benefit.

The method includes administering to the patient in need thereof an effective amount of Compound I, and any of its forms as described herein, or a composition comprising Compound I, and any of its forms as described herein.

In some embodiments, the present disclosure provides methods for treating a subject suffering or at risk of a disease or condition mediated by a bromodomain, said method comprising administering to the subject in need thereof an effective amount of Compound I, and any of its forms as described herein, or any of the pharmaceutical compositions thereof described herein, and the disease or condition is a cancer, an autoimmune condition, an inflammatory condition or a combination thereof.

In some embodiments, the diseases or conditions treatable with Compound I, and any of its forms as described herein, include, but are not limited to, a cancer, e.g., hematological, epithelial including lung, breast and colon carcinomas, midline carcinomas, mesenchymal, hepatic, renal, neurological tumors, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In certain embodiments, the cancer treatable with the compounds of the present disclosure is selected from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor. In other embodiments, the cancers or tumors treatable with the compounds of the present disclosure include benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome. In another embodiment, the diseases or conditions treatable with the compounds of the present disclosure include non-small cell lung cancer, small cell lung cancer, ovarian cancer, melanoma, midline carcinomas, breast cancer, lymphomas, neuroblastoma, or castration resistant prostate cancer, myelofibrosis, myelodysplastic syndromes, or acute myeloid leukemia. In another embodiment, the diseases or conditions treatable with the compounds of the present disclosure include non-small cell lung cancer, small cell lung cancer, ovarian cancer, melanoma, neuroblastoma, and castration resistant prostate cancer.

In another embodiment of this disclosure, the disease or condition that can be treated by the compounds of the present disclosure is a lysosomal storage disorder. Non-limiting examples of lysosomal storage disorders include mucolipodosis, alpha-mannosidosis; aspartylglucosaminuria; Batten disease; beta-mannosidosis; cystinosis; Danon disease; Fabry disease; Farber disease; fucosidosis; galactosialidosis; Gaucher disease; gangliosidosis (e.g., GM1 gangliosidosis and GM2-gangliosidosis AB variant); Krabbe disease; metachromatic leukodystrophy; mucopolysaccharidoses disorders (e.g., MPS 1—Hurler syndrome, MPS II—Hunter syndrome, MPS III—Sanfilippo (A,B,C,D), MPS IVA—Morquio, MPS IX—hyaluronidase, deficiency, MPS VI—Maroteaux-Lamy, or MPS VII—Sly syndrome); mucolipidosis type I (Sialidosis); Mucolipidosis type II (I-Cell disease); Mucolipidosis type III (Pseudo-Hurler polydystrophy); Mucolipidosis type IV; multiple sulfatase deficiency; Niemann-Pick types A, B, C; Pompe disease (glycogen storage disease); pycnodysostosis; Sandhoff disease; Schindler disease; Salla disease/sialic acid storage disease; Tay-Sachs; and Wolman disease.

In some embodiments, the present disclosure provides methods for treating an autoimmune and inflammatory disease or condition in a subject by administration of an effective amount of Compound I, and any of its forms as described herein, or any of the pharmaceutical compositions thereof described herein. The diseases or conditions treatable with the compounds of the present disclosure include, but are not limited to, inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease. In certain embodiments, the diseases and conditions treatable with the compounds of the present disclosure include systemic or tissue inflammation, inflammatory responses to infection or hypoxia, cellular activation and proliferation, lipid metabolism, fibrosis and viral infections.

In some embodiments, the present disclosure provides methods for treating a subject suffering or at risk of chronic autoimmune and inflammatory conditions by administering to the subject in need thereof an effective amount of Compound I, and any of its forms as described herein, or any of the pharmaceutical compositions thereof described herein. The chronic autoimmune and inflammatory conditions treatable with the compounds of the present disclosure include, but are not limited to, rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs. In one embodiment, the disease or condition is sepsis, burns, pancreatitis, major trauma, hemorrhage or ischemia. In another embodiment, the disease or condition treatable with the compounds of the present disclosure includes sepsis, sepsis syndrome, septic shock or endotoxaemia. In another embodiment, the disease or condition treatable with the compounds of the present disclosure includes acute or chronic pancreatitis. In another embodiment, the disease or condition treatable with the compounds of the present disclosure includes burns.

In some embodiments, the present disclosure provides methods for treating a subject suffering or at risk of acute inflammatory conditions by administering to the subject in need thereof an effective amount of Compound I, and any of its forms as described herein, or any of the pharmaceutical compositions thereof described herein. The acute inflammatory conditions, include, but are not limited to, acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

In some embodiments, the present disclosure provides methods for treating a subject suffering or at risk of autoimmune and inflammatory diseases or conditions by administering to the subject in need thereof an effective amount of Compound I, and any of its forms as described herein, or any of the pharmaceutical compositions thereof described herein. The autoimmune and inflammatory diseases or conditions treatable with the compounds of the present disclosure which involve inflammatory responses to infections with bacteria, viruses, such as herpes virus, human papilloma virus, adenovirus and poxvirus and other DNA viruses; fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

In some embodiments, the present disclosure provides methods for treating a subject suffering or at risk of ischemia-reperfusion injury by administering to the subject in need thereof an effective amount of Compound I, and any of its forms as described herein, or any of the pharmaceutical compositions thereof described herein. The ischemia-reperfusion injury, includes, but is not limited to, myocardial infarction, cerebro-vascular ischemia (stroke), acute coronary syndromes, renal reperfusion injury, organ transplantation, coronary artery bypass grafting, cardio-pulmonary bypass procedures, pulmonary, renal, hepatic, gastro-intestinal and peripheral limb embolism.

In some embodiments, the present disclosure provides methods for treating a subject suffering or at risk of hypercholesterolemia, atherosclerosis or Alzheimer's disease by administering to the subject in need thereof an effective amount of Compound I, and any of its forms as described herein, or any of the pharmaceutical compositions thereof described herein.

In some embodiments, the present disclosure provides methods for treating any bromodomain mediated disease or condition, including any bromodomain mutant mediated disease or condition in an animal subject in need thereof, wherein the method involves administering to the subject an effective amount of any one or more compound(s) as described herein or any pharmaceutical compositions thereof described herein. In certain embodiments, the method involves administering to the subject an effective amount of any one or more compound(s) as described herein or any pharmaceutical compositions thereof described herein in combination with one or more other therapies or therapeutic agents for the disease or condition.

In some embodiments, Compound I, and any of its forms as described herein, is a bromodomain inhibitor and has an $IC_{50}$ of less than 500 nM, less than 100 nM, less than 50 nM, less than 20 nM, less than 10 nM, less than 5 nM, or less than 1 nM as determined in a generally accepted bromodomain activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to bromodomain, e.g., BET protein, BRD2, BRD3 or BRD4 protein. In some embodiments, a compound as described herein will selectively inhibit one or more bromodomain relative to one or more other proteins.

In some embodiments, the present disclosure provides a method for inhibiting a bromodomain or mutant bromodomain. The method includes contacting Compound I, and any of its forms as described herein, or any of the pharmaceutical compositions thereof described herein, with a cell or a bromodomain protein in vitro or in vivo.

In certain embodiments, the present disclosure provides use of Compound I, and any of its forms as described herein, or any of the pharmaceutical compositions thereof described herein in the manufacture of a medicament for the treatment of a disease or condition as described herein. In other embodiments, the present disclosure provides Compound I, and any of its forms as described herein, or any of the pharmaceutical compositions thereof described herein for use in treating a disease or condition as described herein.

Combination Therapy

Bromodomain modulators may be usefully combined with another pharmacologically active compound, or with two or more other pharmacologically active compounds, particularly in the treatment of cancer and other diseases and indications described herein. In one embodiment, the composition comprises Compound I, and any of its forms as described herein, along with one or more compounds that are therapeutically effective for the same disease indication, wherein the compounds have a synergistic effect on the disease indication. In one embodiment, the composition comprises Compound I, and any of its forms as described herein, effective in treating a cancer and one or more other compounds that are effective in treating the same cancer, further wherein the compounds are synergistically effective in treating the cancer.

In some embodiments, the present disclosure provides methods for treating a bromodomain or mutant bromodomain mediated disease or condition in an animal subject in need thereof, wherein the method involves administering to the subject an effective amount of Compound I, and any of its forms as described herein, or any of the pharmaceutical compositions thereof described herein, in combination with one or more other therapeutic agent as described herein. In certain embodiments, the present disclosure provides methods for treating bromodomain or mutant bromodomain mediated disease or condition in an animal subject in need thereof, wherein the method involves administering to the subject an effective amount of Compound I, and any of its forms as described herein, or any of the pharmaceutical compositions thereof described herein, in combination with one or more other therapies for the disease or condition.

In another embodiment, the present disclosure provides a composition, e.g., a pharmaceutical composition comprising Compound I, and any of its forms as described herein, or any of the pharmaceutical compositions thereof described herein, and one or more other therapeutic agents selected from the group consisting of i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; xviii) a c-Kit mutant inhibitor, xix) an EGFR inhibitor, or xx) an epigenetic modulator. In further embodiments, a bromodomain modulator, Compound I, and any of its forms as described herein, may be administered simultaneously, sequentially or separately in combination with one or more agents as described above.

Epigenetic modulators include DNA methylating agents and agents that modulate posttranslational modification of histones and/or proteins by the activity of chromatin modifiers. Non-limiting examples of Epigenetic modulators include:

(a) DNA methyltransferases (for example, azacytidine, decitabine or zebularine);

(b) histone and protein methyltransferases, including, but not limited to, DOT1L inhibitors such as EPZ004777 (7-[5-Deoxy-5-[[3-[[[[4-(1,1-dimethylethyl)phenyl]amino]carbonyl]amino]propyl](1-methylethyl)amino]-β-D-ribofuranosyl]-7H-pyrrolo[2,3-d]pyrimidin-4-amine), EZH1 inhibitors, EZH2 inhibitors or EPX5687;

(c) histone demethylases;

(d) histone deacetylase inhibitors (HDAC inhibitors) including, but not limited to, vorinostat, romidepsin, chidamide, panobinostat, belinostat, valproic acid, mocetinostat, abexinostat, entinostat, resminostat, givinostat, or quisinostat;

(e) histone acetyltransferase inhibitors (also referred to as HAT inhibitors) including, but not limited to, C-646, (4-[4-[[5-(4,5-Dimethyl-2-nitrophenyl)-2-furanyl]methylene]-4,5-dihydro-3-methyl-5-oxo-1H-pyrazol-1-yl]benzoic acida), CPTH2 (cyclopentylidene-[4-(4'-chlorophenyl)thiazol-2-yl] hydrazine), CTPB (N-(4-chloro-3-trifluoromethyl-phenyl)-2-ethoxy-6-pentadecyl-benzamide), garcinol ((1R,5R,7R)-3-(3,4-Dihydroxybenzyol)-4-hydroxy-8,8-dimethyl-1,7-bis (3-methyl-2-buten-1-yl)-5-[(2S)-5-methyl-2-(1-methylethenyl)-4-hexen-1-yl]bicyclo[3.3.1]non-3-ene-2,9-dione), anacardic acid, EML 425 (5-[(4-hydroxy-2,6-dimethylphenyl)methylene]-1,3-bis(phenylmethyl)-2,4,6 (1H,3H,5H)-pyrimidinetrione), ISOX DUAL ([3-[4-[2-[5-(Dimethyl-1,2-oxazol-4-yl)-1-[2-(morpholin-4-yl)ethyl]-1H-1,3-benzodiazol-2-yl]ethyl]phenoxy]propyl] dimethylamine), L002 (4[O-[(4-methoxyphenyl)sulfonyl] oxime]-2,6-dimethyl-2,5-cyclohexadiene-1,4-dione), NU 9056 (5-(1,2-thiazol-5-yldisulfanyl)-1,2-thiazole), SI-2 hydrochloride (1-(2-pyridinyl)ethanone 2-(1-methyl-1H-benzimidazol-2-yl)hydrazone hydrochloride); or (f) other chromatin remodelers.

In another embodiment, the epigenetic modulator is vorinostat, romidepsin, belinostat, or panobinostat.

In some embodiments, the present disclosure provides methods for treating a disease or condition mediated by bromodomain, including any mutations thereof, by administering to a subject an effective amount of a composition as described herein, which includes Compound I, and any of its forms as described herein, in combination with one or more other therapeutic agents as described herein. In other embodiments, the present disclosure provides methods for treating a disease or condition mediated by bromodomain protein or mutant bromodomain protein, including any mutations thereof, by administering to a subject an effective amount of a composition as described herein, which Compound I, and any of its forms as described herein, in combination with one or more other suitable therapies for treating the disease or condition. In one embodiment, the present disclosure provides methods for treating a cancer mediated by bromodomain or mutant bromodomain by administering to the subject an effective amount of a composition including Compound I, and any of its forms as described herein. In one embodiment, the present disclosure provides methods for treating a cancer mediated by bromodomain by administering to the subject an effective amount of a composition including Compound I, and any of its forms as described herein, in combination with one or more suitable anticancer therapies, such as one or more chemotherapeutic drugs or agents as described herein.

In some embodiments, compositions are provided that include a therapeutically effective amount of Compound I, and any of its forms as described herein, and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include Compound I, and any of its forms as described herein, along with one or more compounds that are therapeutically effective for the same disease indication. In one aspect, the composition includes Compound I, and any of its forms as described herein, along with one or more compounds that are therapeutically effective for the same disease indication, wherein the compounds have a synergistic effect on the disease indication. In one embodiment, the composition includes Compound I, and any of its forms as described herein, effective in treating a cancer and one or more other compounds that are effective in treating the same cancer, further wherein the compounds are synergistically effective in treating the cancer. The compounds can be administered simultaneously or sequentially.

In some embodiments, the present disclosure provides a composition, e.g., a pharmaceutical composition comprising Compound I, and any of its forms as described herein, in combination with a FLT3 inhibitor, such as quizartinib.

In one embodiment, the present disclosure provides methods for treating a disease or condition mediated by bromodomain or mutant bromodomain protein, by administering to the subject an effective amount of Compound I, and any of its forms as described herein, and quizartinib for treating the disease or condition.

In some embodiments, the disclosure provides a method of treating a subject suffering from a disease or condition described in this disclosure, said method comprising administering to the subject an effective amount of Compound I, and any of its forms as described herein, in combination with a mutant c-Kit protein kinase inhibitor. In another embodiment, the mutant c-Kit protein kinase inhibitor is selected from (2-phenyl-1H-pyrrolo[2,3-b]pyridin-5-yl)-(3-pyridyl) methanol, (2-phenyl-1H-pyrrolo[2,3-b]pyridin-5-yl)-(3-pyridyl)methanone, N-(3-carbamoylphenyl)-2-phenyl-1H-pyrrolo[2,3-b]pyridine-5-carboxamide, 2-phenyl-N-(1H-pyrazol-3-yl)-1H-pyrrolo[2,3-b]pyridine-5-carboxamide, 4-bromo-N-(2-phenyl-1H-pyrrolo[2,3-b]pyridin-5-yl)-1H-pyrazole-5-carboxamide, ethyl 3-[(2-phenyl-1H-pyrrolo[2,3-b]pyridin-5-yl)carbamoylamino]propanoate, 3,4-dimethyl-N-(2-phenyl-1H-pyrrolo[2,3-b]pyridin-5-yl)-1H-pyrazole-5-carboxamide, 4-methyl-3-phenyl-N-(2-phenyl-1H-pyrrolo[2,3-b]pyridin-5-yl)-1H-pyrazole-5-carboxamide, 3-cyclopropyl-N-(2-phenyl-1H-pyrrolo[2,3- b]pyridin-5-yl)-1H-pyrazole-5-carboxamide, 5-fluoro-N-(2-phenyl-1H-pyrrolo[2,3-b]pyridin-5-yl)-1H-indazole-3-carboxamide, N-(2-phenyl-1H-pyrrolo[2,3-b]pyridin-5-yl) pyrimidine-4-carboxamide, 3-fluoro-N-(2-phenyl-1H-pyrrolo[2,3-b]pyridin-5-yl)pyridine-2-carboxamide, 3,5-dimethyl-N-(2-phenyl-1H-pyrrolo[2,3-b]pyridin-5-yl) isoxazole-4-carboxamide, N-(2-phenyl-1H-pyrrolo[2,3-b]pyridin-5-yl)pyridazine-3-carboxamide, N-(2-phenyl-1H-pyrrolo[2,3-b]pyridin-5-yl)-2H-triazole-4-carboxamide, 3-methyl-N-(2-phenyl-1H-pyrrolo[2,3-b]pyridin-5-yl)pyridine-2-carboxamide, 4,5-dimethyl-N-(2-phenyl-1H-pyrrolo[2,3-b]pyridin-5-yl)isoxazole-3-carboxamide or N-(2-phenyl-1H-pyrrolo[2,3-b]pyridin-5-yl)-1H-pyrazole-4-sulfonamide. In another embodiment, Compound I, and any of its forms as described herein, is combined with any of the mutant c-Kit mutant inhibitors described in this specification for treating GIST—which includes, without limitation, $1^{st}$ line, $2^{nd}$ line and neoadjuvant GIST.

In some embodiments, the present disclosure provides a method of treating a cancer as described herein in a subject in need thereof by administering to the subject an effective amount of Compound I, and any of its forms as described herein, or a composition including Compound I, and any of its forms as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the present disclosure provides a method of treating a cancer in a subject in need thereof by administering to the subject an effective amount of Compound I, and any of its forms as described herein, and applying a radiation treatment as described herein either separately or simultaneously. In one embodiment, the present disclosure provides a method for treating a cancer in a subject in need thereof by administering an effective amount of Compound I, and any of its forms as described herein, to the subject followed by a radiation treatment (e.g. x-ray, γ-ray, or electron, proton, neutron, or α particle beam). In another embodiment, the present disclosure provides a method for treating a cancer in a subject in need thereof by applying a radiation treatment (e.g. x-ray, γ-ray, or electron, proton, neutron, or α particle beam) to the subject followed by administering an effective amount of Compound I, and any of its forms as described herein, to the subject. In yet another embodiment, the present disclosure provides a method for treating a cancer in a subject in need thereof by administering Compound I, and any of its forms as described herein, and a radiation therapy (e.g. x-ray, γ-ray, or electron, proton, neutron, or α particle beam) to the subject simultaneously.

EXAMPLES

Instrumental Techniques

X-Ray Powder Diffraction

For XRPD analyses provided herein, a PANalytical Empyrean X-ray powder diffract meter was used, and the XRPD parameters used are summarized in Table 1.

TABLE 1

Parameters for XRPD test

| Parameters | XRPD (Reflection Mode) |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0130 |
| Scan speed (°/min) | About 7 |

Differential Scanning Calorimetery and Thermogravimetric Analysis

DSC was performed using a TA Q200/Q2000 DSC from TA Instruments. TGA data were collected using a TA Q500/Q5000 TGA from TA Instruments. Detailed parameters used are listed in Table 2.

TABLE 2

Parameters for TGA and DSC test

| Parameters | TGA | DSC |
|---|---|---|
| Method | Ramp | Ramp |
| Sample pan | Platinum, open | Aluminum, crimped |
| Temperature | RT - desired temperature | 25° C. - desired temperature |
| Heating rate | 10° C./min | 10° C./min |
| Purge gas | $N_2$ | $N_2$ |

Dynamic Vapor Sorption

DVS was measured via a SMS (Surface Measurement Systems) DVS Intrinsic. The relative humidity at 25° C. were calibrated against deliquescence point of LiCl, $Mg(NO_3)_2$ and KCl. Actual parameters for DVS test are listed in Table 3.

TABLE 3

Parameters for DVS test

| Parameters | DVS |
|---|---|
| Temperature | 25° C. |
| Sample size | 10~20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH to 95% RH |
| RH step size | 10% RH from 0% RH to 90% RH 5% RH from 90% RH to 95% RH |

Example 1. Synthesis of Compound I

Compound I may be synthesized according to Scheme 1.

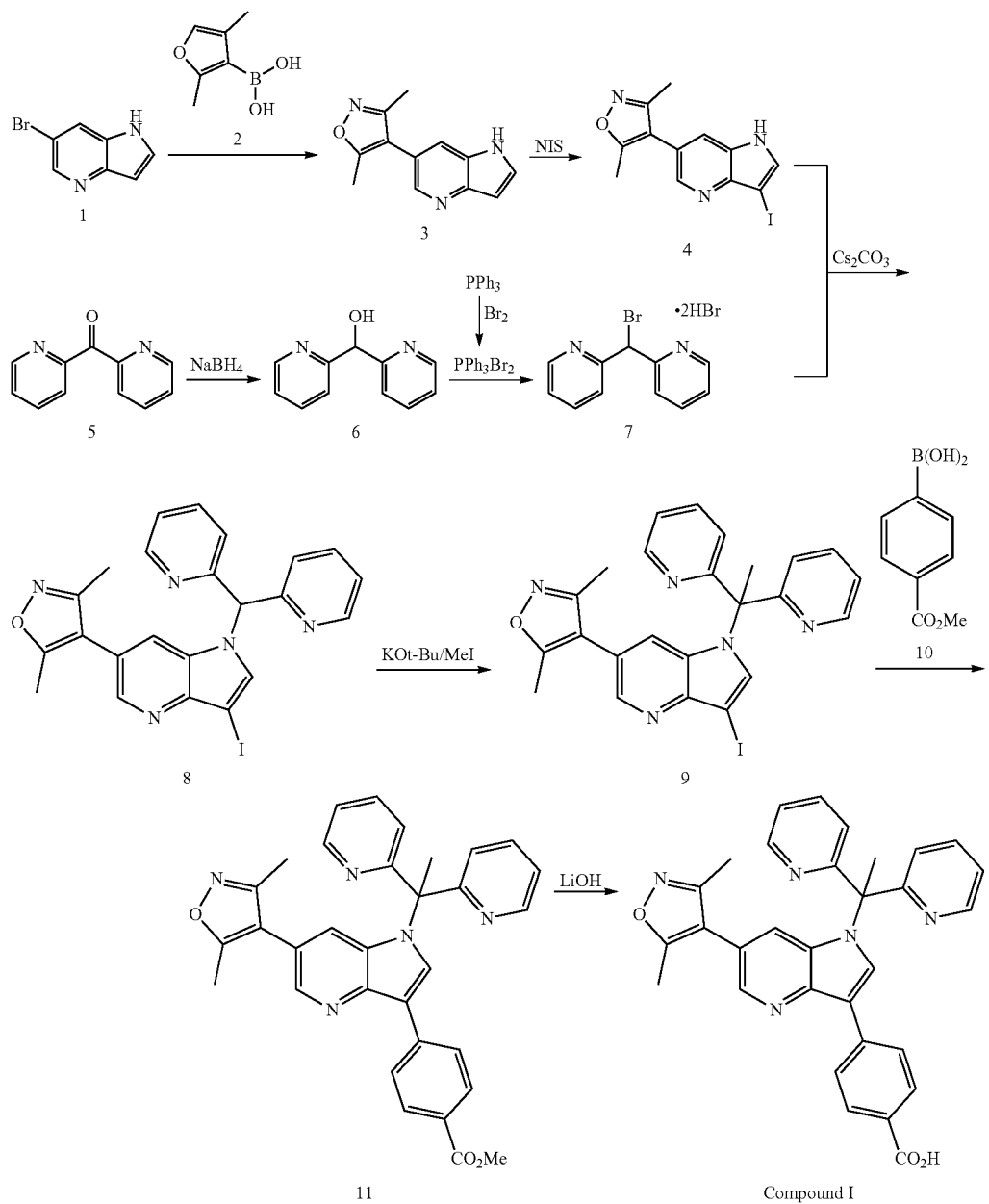

3,5-Dimethyl-4-(1H-pyrrolo[3,2-b]pyridin-6-yl)isoxazole (3)

A suspension of 6-bromo-1H-pyrrolo[3,2-b]pyridine 1 (450 g, 2.284 mol, 1 equiv), (3,5-dimethylisoxazol-4-yl) boronic acid 2 (418 g, 2.969 mol, 1.3 equiv), potassium carbonate (947 g, 6.852 mol, 3 equiv) and bis(triphenylphosphine)palladium(II) dichloride (80 g, 114 mmol, 0.05 equiv) in dioxane (6.5 L) and water (2 L) was sparged with nitrogen for 10 minutes. The reaction mixture was heated at 90° C. overnight, at which point LC/MS indicated the reaction was complete. The reaction was diluted with ethyl acetate (8 L) and water (8 L). The layers were separated and the organic layer was passed through silica gel (1 Kg) rinsing with additional ethyl acetate (4 L). Another run of the same size was combined and the filtrate was concentrated under reduced pressure to give compound 2 which was used subsequently in the next step.

4-(3-Iodo-1H-pyrrolo[3,2-b]pyridin-6-yl)-3,5-dimethylisoxazole (4)

N-Iodosuccinimide (1130 g, 5.024 mol, 1.1 equiv) was added to a solution of compound 2 (974 g theory, 4568 mmol, 1 equiv) in acetonitrile (28 L) and dimethyl acetamide (3 L). The reaction was stirred overnight at room temperature, at which point LC/MS indicated the reaction was complete. The acetonitrile was removed under reduced pressure and the residue was slurried in a mixture of warm water (20 L) and saturated sodium thiosulfate (4 L). The solid was collected by filtration and washed with additional water (4 L). The crude solid was triturated with MTBE (4 L) to give compound 4 (1360 g, 88% yield) after drying in a convection oven at 50° C. for three days.

Di(pyridin-2-yl)methanol (6)

Sodium borohydride (37.0 g, 979 mmol, 0.36 equiv) was added in portions to a solution of compound 5 (500. g, 2710 mmol, 1 equiv) in methanol (10 L) at 0° C. The reaction was allowed to stir for 1.5 hours at which point LC/MS indicated full consumption of compound 5. The solution was concentrated under reduced pressure. The residue was dissolved in 1 N hydrochloric acid (2 L). The pH was adjusted to about 8 with solid sodium bicarbonate (226 g). The solution was extracted twice with ethyl acetate (2×4 L). The combined organic layers were dried over sodium sulfate and concentrated under reduced pressure to give compound 6 (484 g, 96% yield).

Triphenylphosphine Dibromide:

A solution of bromine (98 mL, 1906 mmol, 1 equiv) in dichloromethane (200 mL) was added dropwise to a solution of triphenylphosphine (500 g, 1906 mmol, 1 equiv) in dichloromethane (1.5 L) keeping the internal temperature<10° C. with the aid of an ice bath. After the addition was complete, the reaction was allowed to warm to room temperature and stirred for 1 hour. Stirring was stopped and the supernatant was decanted and concentrated under reduced pressure to a heel and transferred back to the original flask. Stirring was resumed and MTBE (about 2 L) was added and the slurry was filtered washing with additional MTBE (about 1 L). The solid was dried in the filter under a blanket of nitrogen for 1 hour to give the desired product (920 g) was used subsequently in the next step.

2,2'-(Bromomethylene)dipyridine dihydrobromic acid (7)

Compound 6 (118 g, 636 mmol, 1 equiv) was dissolved in dichloromethane (2.4 L), cooled to 0° C., and sparged with nitrogen for 30 minutes. Triphenylphosphine dibromide from above (805 g theory, 1.9 mol, 3 equiv) was then added slowly. The reaction was warmed to room temperature and stirred overnight. The solution was concentrated under reduced pressure and the residue was dissolved in toluene (2.5 L) and water (4.5 L). The layers were separated, the organic layer was discarded. The aqueous layer was washed with toluene (2×2 L). The pH of the aqueous layer was adjusted to ~8 with solid sodium bicarbonate (337 g). The aqueous layer was extracted with DCM (3×1 L). The combined organic layers were concentrated under reduced pressure to give free based compound 7 (126 g, 80% yield).

4-(1-(Di(pyridin-2-yl)methyl)-3-iodo-1H-pyrrolo[3,2-b]pyridin-6-yl)-3,5-dimethylisoxazole (8)

Compound 4 (57.4 g, 169 mmol, 1 equiv), free based compound 7 (67.4 g, 271 mmol, 1.6 equiv) and cesium carbonate (127 g, 389 mmol, 2.3 equiv) were dissolved in THF (1.5 L) and refluxed overnight. The reaction mixture was combined with two other batches of compound 4 (66.3 g combined). The mixture was diluted with saturated brine (3.3 L). The organic layer was separated and concentrated under reduced pressure. The residue was purified over silica gel (2 kg), eluting with a gradient of 0 to 100% ethyl acetate in dichloromethane. The material was triturated with MTBE (2 L) to give compound 8 (104.6 g, 58% yield).

4-(1-(1,1-Di(pyridin-2-yl)ethyl)-3-iodo-1H-pyrrolo[3,2-b]pyridin-6-yl)-3,5-dimethylisoxazole (9)

Potassium tert-butoxide (30.4 g, 247 mmol, 1.2 equiv) was added in portions to a solution of compound 8 (104.4 g, 206 mmol, 1 equiv) and iodomethane (38.5 mL, 617 mmol, 3 equiv) in anhydrous THF (2.1 L). The reaction was allowed to stir at room temperature overnight. The solution was quenched with saturated brine (2 L). The organic layer was separated and concentrated under reduced pressure. The residue was purified over silica gel (2 kg) eluting with a gradient of 0 to 40% ethyl acetate in dichloromethane to give compound 9 (97.0 g, 90% yield).

Methyl 4-(1-(1,1-di(pyridin-2-yl)ethyl)-6-(3,5-dimethylisoxazol-4-yl)-1H-pyrrolo[3,2-b]pyridin-3-yl)benzoate (11)

A mixture of compound 9 (92.7 g, 178 mmol, 1 equiv), compound 10 (64.0 g, 356 mmol, 2 equiv), and potassium carbonate (73.7 g, 534 mmol, 3 equiv) in dioxane (1 L) and water (330 mL) were sparged with nitrogen for 15 minutes. [1,1'-bis(diphenylphosphino)ferrocene] dichloropalladium (II) (7.8 g, 11 mmol, 0.06 equiv) was added and the reaction was heated at 80° C. overnight. After cooling to room temperature, the solution was diluted with ethyl acetate (1 L) and water (1 L). The organic layer was separated and concentrated under reduced pressure. The residue was purified over silica gel (1 kg), eluting with a gradient of 0 to 100% ethyl acetate in dichloromethane. The clean fractions were triturated with MTBE (500 mL) to give compound 11 (90.7 g, 96% yield).

4-(1-(1,1-Di(pyridin-2-yl)ethyl)-6-(3,5-dimethylisoxazol-4-yl)-1H-pyrrolo[3,2-b]pyridin-3-yl)benzoic acid (Compound I)

A 2 M solution of lithium hydroxide (2.4 L, 4.8 mol, 15 equiv) was added to a solution of compound 11 (169 g, 319 mmol, 1 equiv) in THF (5 L). After heating at 55° C. overnight, the reaction was cooled to room temperature and diluted with saturated brine (2.5 L). The pH was adjusted to about 5 with 1 N HCl (3.45 L) and diluted with ethyl acetate (5 L). The organic layer was separated, washed with saturated brine (2.5 L) and concentrated under reduced pressure. The residue was dissolved in dichloromethane (2 L) and filtered. The filtrate was diluted with acetonitrile (1 L) and concentrated under reduced pressure to a volume of about 750 mL. The resulting suspension was filtered and the solids were dried under vacuum at 60° C. overnight to give Compound I (137 g, 84% yield).

Example 2. Polymorph Screening

Polymorph screening experiments were performed using the following different crystallization or solid transition methods.

Anti-Solvent Addition

A total of 7 anti-solvent addition experiments were carried out. About 10 mg of Compound I Form A, prepared as described above, was dissolved in 0.2-2.5 mL solvent to obtain a clear solution. The solution was magnetically stirred followed by addition of 0.2 mL anti-solvent per step until precipitate appeared or the total amount of anti-solvent reached 15.0 mL. The obtained precipitate was isolated for XRPD analysis. Results, which are summarized in Table 4, show Form A and Form E were obtained.

TABLE 4

Summary of anti-solvent addition experiments

| Solvent | Anti-solvent | Solid Form |
|---|---|---|
| Acetone | H$_2$O | Form A + E |
| THF | H$_2$O | Form A |
| 2-MeTHF | n-heptane | Form A + E |
| 1,4-dioxane | Toluene | Form A |
| DCM | n-heptane | Form A + E |
| CHCl$_3$ | MTBE* | Form A + E |
| EtOAc | Toluene* | Form A |

*no solid was obtained via stirring the clear solution at 5° C. or −20° C. therefore evaporation was applied.

Slow Evaporation

Slow evaporation experiments were performed under five conditions. Briefly, about 8 mg of Compound I Form A was dissolved in 1.0 mL of solvent in a 3-mL glass vial. If no dissolution was achieved, suspensions were filtered using a nylon membrane (pore size of 0.45 μm) and the filtrates were used for the following steps. The visually clear solutions were covered by Parafilm® with 3-4 pinholes and subjected to evaporation at RT. The solids were isolated for XRPD analysis. The results are summarized in Table 5.

TABLE 5

Summary of slow evaporation experiments

| Solvent | Solid Form |
|---|---|
| Acetone | Form A + C |
| THF | Amorphous |
| 2-MeTHF | Gel |
| DCM | Gel |
| CHCl$_3$ | Gel |

Solid Vapor Diffusion

Solid vapor diffusion experiments were conducted with six different solvents. Approximate 8 mg of Compound I Form A was weighed into a 3-mL vial, and placed into a 20-mL vial with 2 mL of volatile solvent. The 20-mL vial was sealed with a cap and kept at RT for about one week to allow interaction of solvent vapor with sample. The solids were tested by XRPD and the results, which are summarized in Table 6, showed that Form A, C and D were observed.

TABLE 6

Summary of solid vapor diffusion experiments

| Solvent | Solid Form |
|---|---|
| H$_2$O | Form A |
| Acetone | Form C |
| MeOH | Form A |
| ACN | Form A |
| 2-MeTHF | Form A |
| DMF | Form D |

Liquid Vapor Diffusion

Four liquid vapor diffusion experiments were conducted. Approximate 10 mg of Compound I Form A was dissolved in appropriate solvent to obtain a clear solution in a 3-mL vial. This solution was then placed into a 20-mL vial with 3 mL of volatile solvents. The 20-mL vial was sealed with a cap and kept at RT to provide sufficient time for interaction of organic vapor with the solution. After about 1 to about 6 days, solids were isolated for XRPD analysis. The results, which are summarized in Table 7, showed that Form A, C and E were observed.

TABLE 7

Summary of liquid vapor diffusion experiments

| Solvent | Anti-solvent | Solid Form |
|---|---|---|
| Acetone | n-heptane | Form C |
| THF | MTBE | Form A |
| EtOAc | n-heptane | Form E |
| CHCl$_3$ | Toluene | Form A |

Slurry at RT

Slurry conversion experiments were conducted at RT in different solvent systems. About 10 mg of Compound I Form A was suspended in 0.5 mL of solvent in a 1.5-mL glass vial. After the suspension was stirred magnetically for 6 days at RT, the remaining solids were isolated for XRPD analysis. Results, which are summarized in Table 8, indicated that only Form A and B were obtained.

TABLE 8

Summary of slurry conversion experiments at RT

| Solvent (v:v) | Solid Form |
|---|---|
| MeOH | Form B |
| EtOH | Form A |
| ACN | Form A |
| EtOAc | Form A |
| MIBK | Form A |
| Acetone/H$_2$O (1:3) | Form A |
| THF/H$_2$O (1:3) | Form A |
| 2-MeTHF/n-heptane (1:3) | Form A |
| 1,4-dioxane/toluene (1:3) | Form A |
| DCM/MTBE (1:3) | Form A |
| H$_2$O | Form A |

Slurry at 50° C.

Slurry conversion experiments were conducted at 50° C. in different solvent systems. About 10 mg of Compound I Form A was suspended in 0.3 mL of solvent in a 1.5-mL glass vial. After the suspension was stirred for about 6 days at 50° C., the remaining solids were isolated for XRPD analysis. Results, which are summarized in Table 9, indicated that Form A and B were obtained.

TABLE 9

Summary of slurry conversion experiments at 50° C.

| Solvent (v:v) | Solid Form |
|---|---|
| MeOH | Form B |
| EtOH | Form A |
| ACN | Form A |
| IPAc | Form A |
| MIBK | Form A |
| Acetone/H$_2$O (1:5) | Form A |
| THF/H$_2$O (1:5) | Form A |
| 2-MeTHF/n-heptane (1:5) | Form A |
| 1,4-dioxane/toluene (1:5) | Form A |
| CHCl$_3$/MTBE (1:5) | Form A |
| H$_2$O | Form A |

Slow Cooling

Slow cooling experiments were conducted in six solvent systems. About 10 mg of Compound I Form A was suspended in 0.5 mL of solvent in a 3-mL glass vial at RT. The suspension was then heated to 50° C., equilibrated for about two hours and filtered using a nylon membrane (pore size of 0.45 μm). Filtrates were slowly cooled down to 5° C. at a rate of 0.1° C./min. No solid was obtained for any system and the solutions were then transferred to −20° C. If no precipitation observed, the solutions were subjected to evaporation at RT. Results summarized in Table 10 indicated Form A, A+B, and A+E were observed.

TABLE 10

Summary of slow cooling experiments

| Solvent (v:v) | Solid Form |
|---|---|
| MeOH | Form A + B |
| ACN | Form A |
| IPAc* | Form A |
| MIBK* | Form A + E |
| Acetone/H$_2$O (1:3)* | N/A |
| 2-MeTHF/n-heptane (1:3)* | N/A |

*no solid was generated after storing solutions at −20° C. for 2 days and then evaporation at RT was employed.
N/A: limited solid for XRPD analysis.

Example 3. Characterization of Solid Forms of Compound I

Compound I Form A

Compound I was prepared according to Example 1. The product was characterized by XRPD, TGA, and DSC and determined to be Compound I Form A. The XRPD of Compound I Form A is shown in FIG. 1. As shown by TGA and DSC data in FIG. 2, Compound I Form A had 1.5% weight loss up to 150° C. and an endothermic peak at 234.2° C. before melting at 266.1° C. (onset temperature). It is contemplated that Compound I Form A is an anhydrate.

Figure 3:
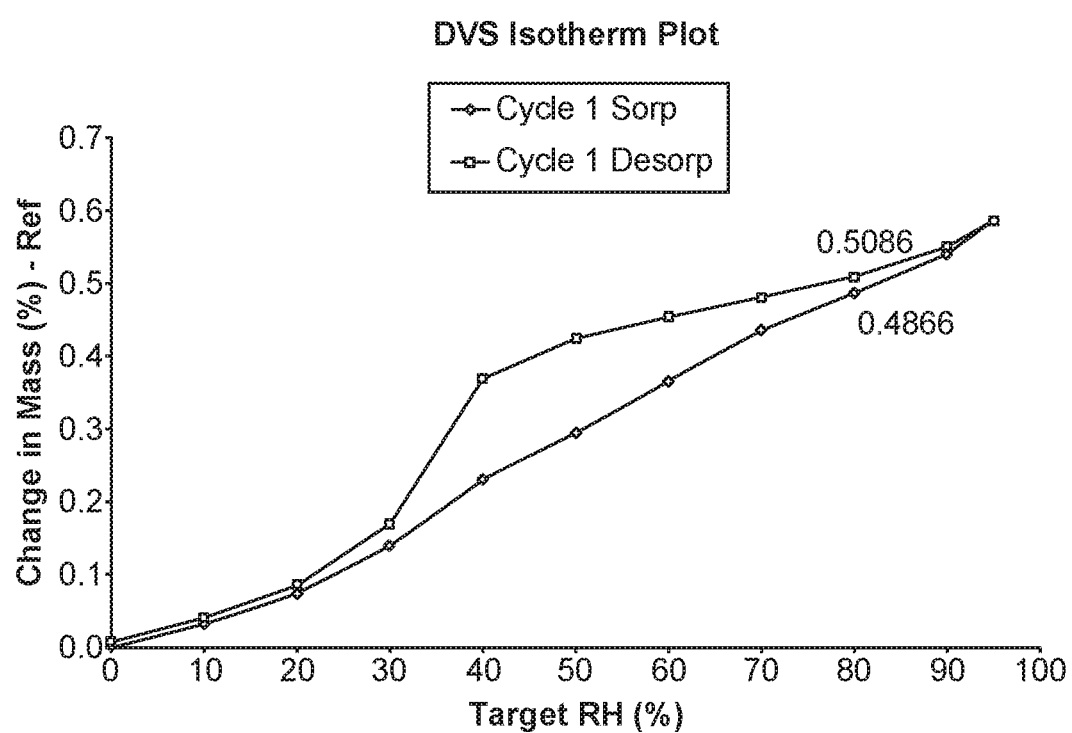
FIG. 3 is a dynamic vapor sorption (DVS plot) of Compound I Form A.

DVS isotherm plot was collected at 25° C. to investigate the solid form stability as a function of humidity for Form A. Solids were pre-dried at 0% RH to remove surface solvent or water before DVS. Water uptake of 0.5% was observed up to 80% RH (FIG. 3), suggesting Compound I Form A may be slightly hygroscopic. No form change was observed after DVS test according to XRPD.

The single crystal of Compound I Form A was obtained from slow evaporation in IPAc at RT. The structure was determined by SCXRD and data analysis. The crystal structural information and refinement parameters are listed in Table 11.

TABLE 11

Structural information and refinement parameters for Compound I Form A single crystal

| Empirical formula | C$_{31}$H$_{25}$N$_5$O$_3$ | |
|---|---|---|
| Formula weight | 515.56 | |
| Temperature | 100 K | |
| Wavelength | Cu/Kα (λ = 1.54178 Å) | |
| Crystal system, space group | Monoclinic, P2$_1$/c | |
| Unit cell dimensions | a = 19.3990(10) Å | α = 90° |
| | b = 8.2109(4) Å | β = 94.057(3)° |
| | c = 16.1667(8) Å | γ = 90° |
| Volume | 2568.6(2) Å$^3$ | |
| Z, Calculated density | 4, 1.333 g/cm$^3$ | |
| 2 Theta range for data collection | 4.566 to 120.094° | |
| Reflections collected/ Independent reflections | 55275/3812 [R(int) = 0.0920] | |

TABLE 11-continued

Structural information and refinement parameters for Compound I Form A single crystal

| Completeness | 99.84% |
|---|---|
| Data/restraints/parameters | 3812/0/356 |
| Goodness-of-fit on F$^2$ | 1.159 |
| Final R indices [I > 2sigma(I)] | R$_1$ = 0.1420, wR$_2$ = 0.3834 |
| Largest diff. peak and hole | 0.77/−0.54 e · Å$^{−3}$ |

Figure 14:
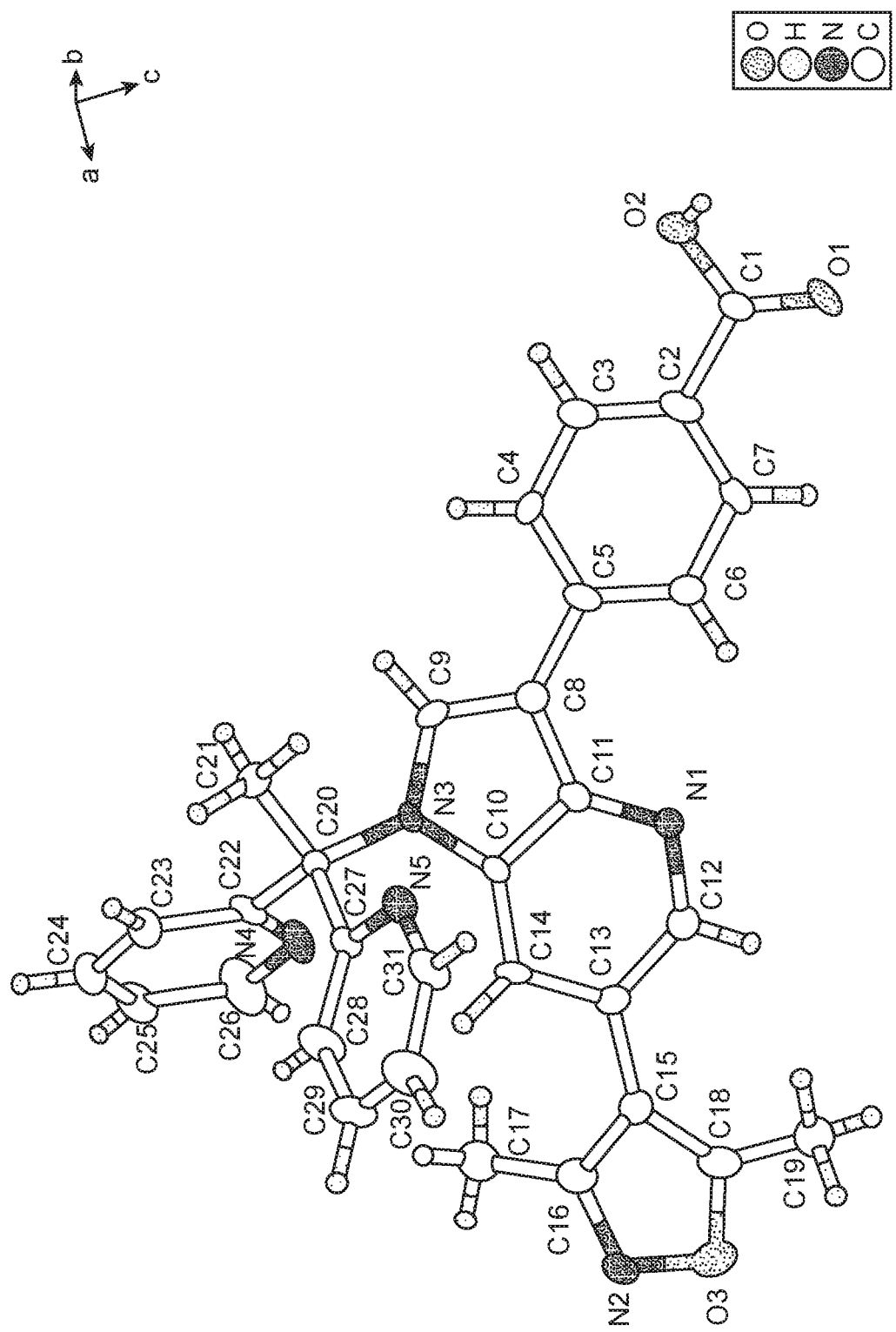
FIG. 14 depicts the asymmetric unit of Compound I Form A single crystal.
Figure 15:
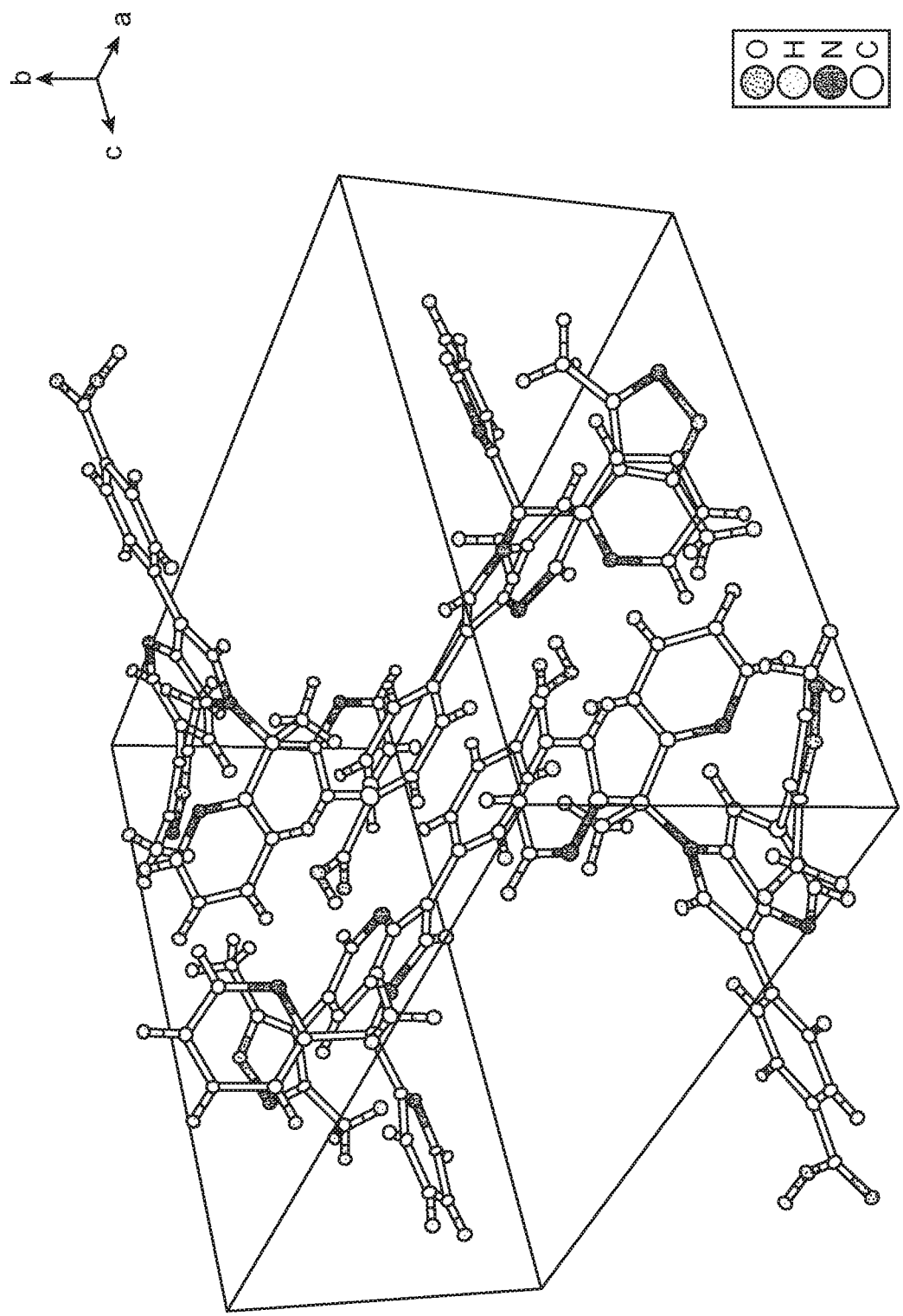
FIG. 15 depicts the unit cell of Compound I Form A single crystal.

The SCXRD characterization and structural analysis suggested that the crystal is in monoclinic crystal system and P2√c space group. The asymmetric unit and the unit cell of the crystal are displayed in FIG. 14 and FIG. 15, respectively. The asymmetric unit is comprised of only one Compound I molecule, indicating the compound is an anhydrate. The bond lengths of the C—O/C═O from the carboxyl group are obviously different (C—O/C═O: 1.342 Å/1.205 Å), indicating that the carboxyl group is not deprotonated. The calculated XRPD pattern of Compound I Form A from single crystal is in agreement with the experimental XRPD pattern (reflection mode).

Compound I Form B

Compound I Form B was generated via slurry in MeOH at 50° C. as discussed above.

Figure 4:
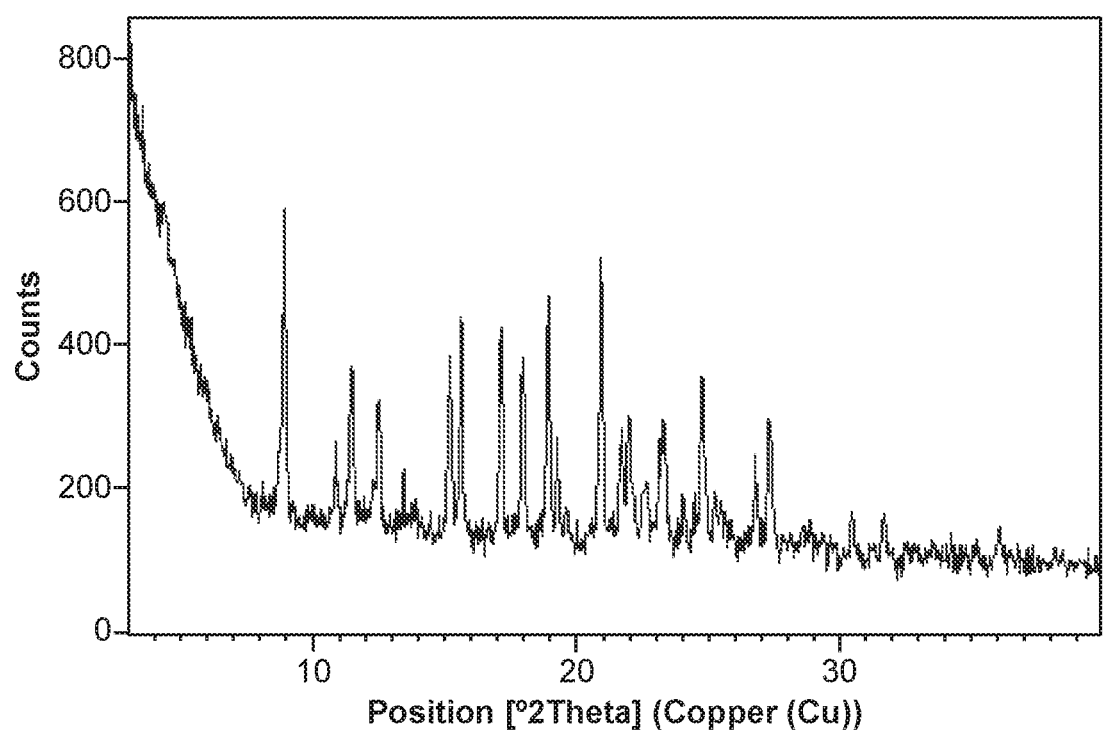
FIG. 4 is an X-ray powder diffractogram of Compound I Form B.
Figure 5:
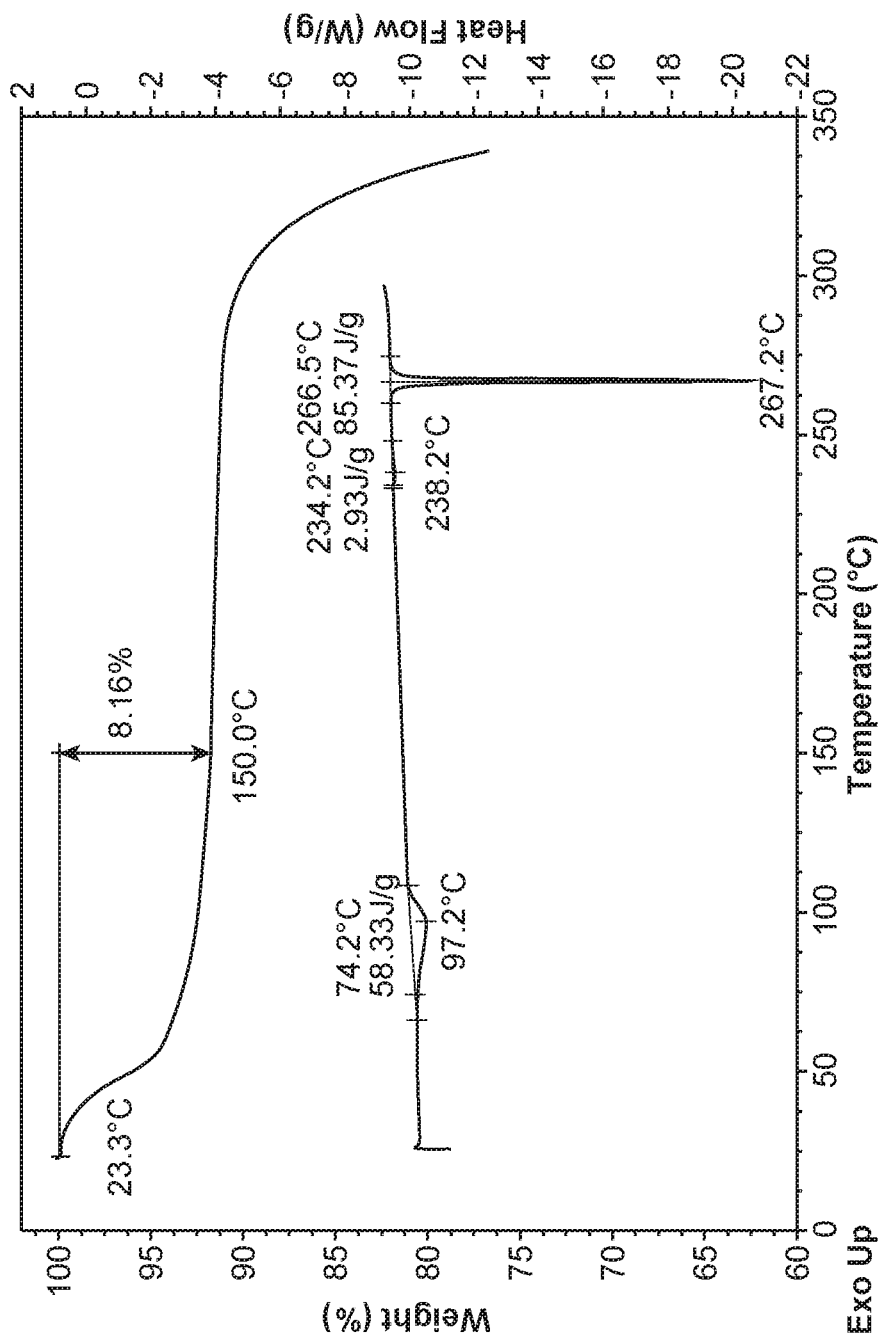
FIG. 5 is a thermogravimetric analysis (TGA) (top line) and a differential scanning calorimeter (DSC) curve (bottom line) of Compound I Form B.

The XRPD pattern of Compound I Form B is displayed in FIG. 4, and TGA and DSC data are shown in FIG. 5. A weight loss of 8.2% was observed up to 150° C. and three endothermic peaks at 74.2° C., 234.2° C. and 266.5° C. (onset temperature) were observed in DSC. XRPD analyses showed that Form B converted to Form A after heating to 110° C.

$^1$H NMR (collected on Bruker 400M NMR Spectrometer using DMSO-d6) detected MeOH content with a molar ratio of 0.34:1 (MeOH/free form). Thus, it is contemplated Compound I Form B may be a MeOH solvate.

Compound I Form C

Figure 6:
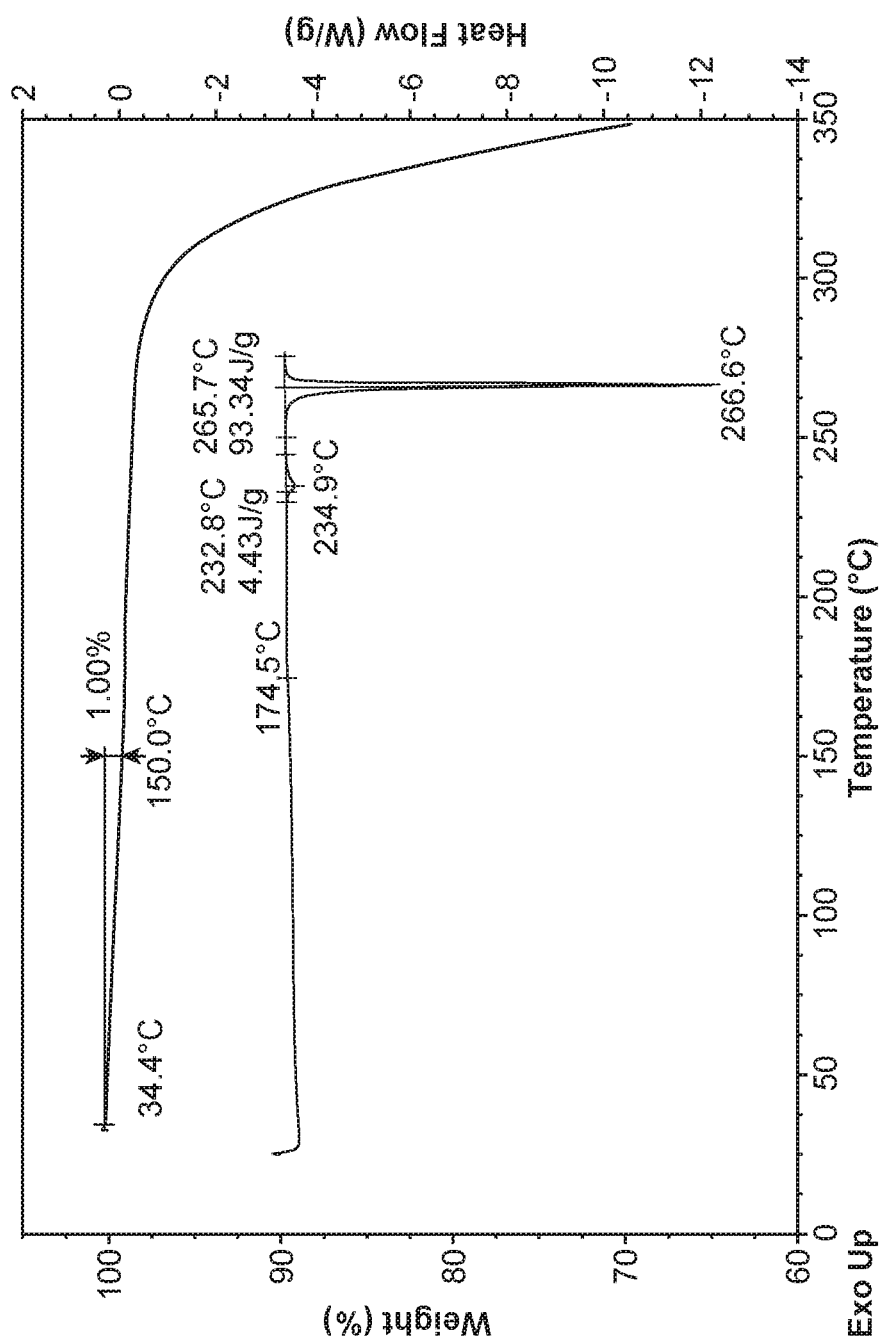
FIG. 6 is a thermogravimetric analysis (TGA) (top line) and a differential scanning calorimeter (DSC) curve (bottom line) of Compound I Form C.

Compound I Form C was prepared via anti-solvent addition in acetone/n-heptane at RT. TGA and DSC data displayed in FIG. 6 indicated a weight loss of 1.0% up to 150° C. and an exotherm at 174.5° C. (peak temperature) followed by two endotherms at 232.8° C. and 265.7° C. (onset temperature). After heating above the exothermic peak, Form C completely converted to Form A as shown by XRPD results. Based on the Burger-Ramberger Rules (Theory of thermodynamic rules, by A. Burger and R. Ramberger, *Mikrochimica Acta*, 1979 II, 259-271), it is contemplated that Compound I Form A is monotropically more stable than Form C before melting. It is also contemplated that Form C may be an anhydrate based on the characterization results.

Compound I Form C was also re-prepared on a 70 mg scale as follows. About 93.5 mg of Compound I Form A was added to 5.0 mL acetone and stirred at 50° C. for 0.5 hr. Then, 7.5 mL n-heptane was added to the acetone solution as anti-solvent, with magnetic stirring at 500 rpm at RT. About 2 mg of Form C seed, made as described above, was added, and the suspension was stirred at RT overnight. The mixture was centrifuged, and the wet cake was dried at ambient conditions overnight, followed by vacuum drying at RT for 1 hr. The solids were collected for the following analyses.

Figure 7:
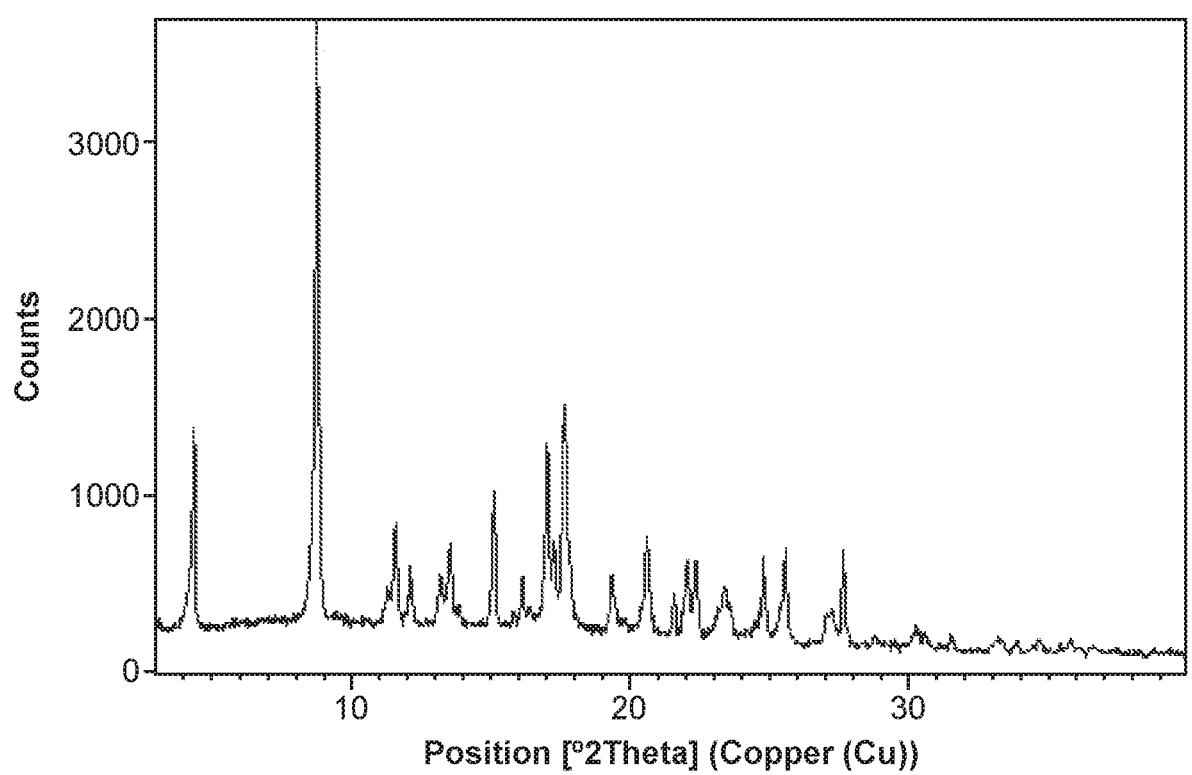
FIG. 7 is an X-ray powder diffractogram of Compound I Form C.
Figure 8:
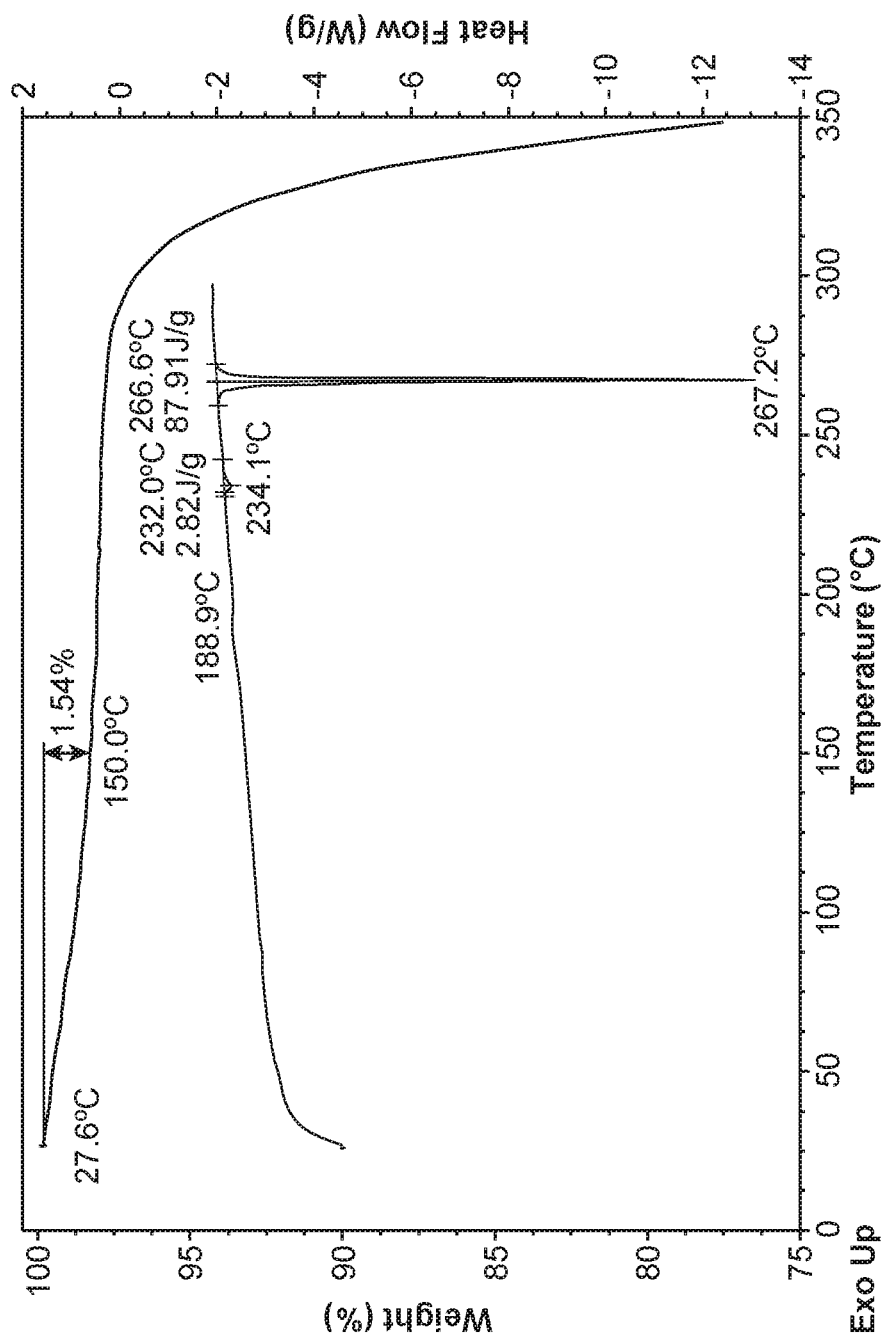
FIG. 8 is a second thermogravimetric analysis (TGA) (top line) and a differential scanning calorimeter (DSC) curve (bottom line) of Compound I Form C.

The XRPD of this sample of Form C is shown in FIG. 7, and TGA/DSC data are shown in FIG. 8. A weight loss of 1.5% was observed up to 150° C. and one exotherm was observed in DSC before two endothermic peaks at 232.0° C. and 266.6° C. (onset temperature).

Figure 9:
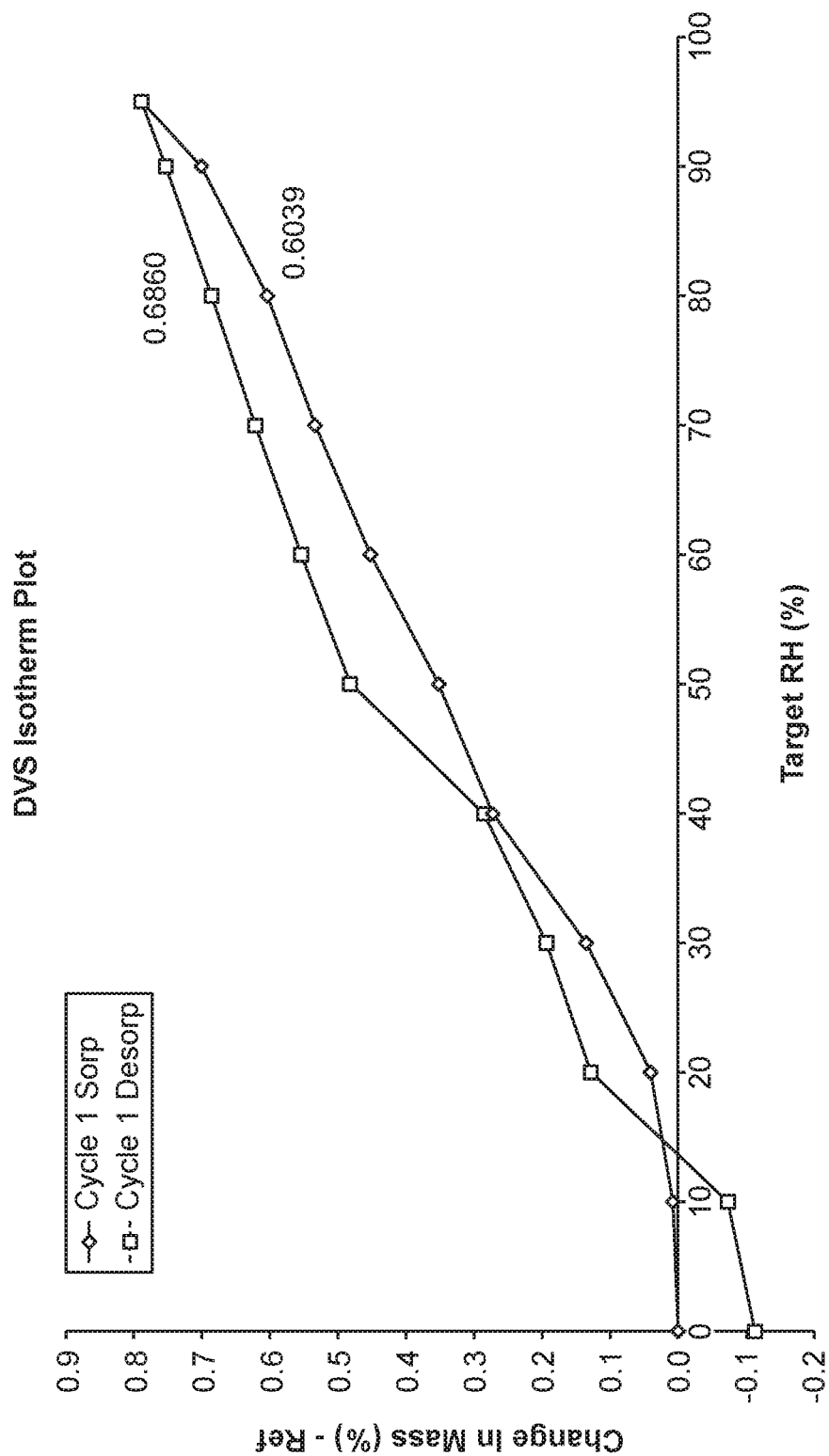
FIG. 9 is a dynamic vapor sorption (DVS plot) of Compound I Form C.

DVS isotherm plot was collected at 25° C. to investigate the solid form stability as a function of humidity for Form C. Solids were pre-dried at 0% RH to remove surface solvent or water before DVS. Water uptake of 0.6% was observed up to 80% RH (FIG. 9). Phase transition of Form C to Form A was noticed from the appearance of possible Form A diffraction peaks after DVS.

Compound I Form D

Compound I Form D was generated via solid vapor diffusion in DMF at RT as discussed above. The XRPD pattern is displayed in FIG. 10. TGA and DSC data shown in FIG. 11 indicated a weight loss of 14.4% up to 150° C., and three endothermic peaks at 104.8° C., 234.3° C. and 266.7° C. (peak temperature) plus one exotherm at 197.3° C. XRPD analysis indicated that Form D converted to Form C after heating to 145° C. and cooling to ambient conditions. $^1$H NMR (collected on Bruker 400M NMR Spectrometer using DMSO-d6) indicated DMF content with a molar ratio of 0.87:1 (DMF/free form). Based on this data, it is contemplated that Compound I Form D may be a DMF solvate.

Compound I Form E

Figure 13:
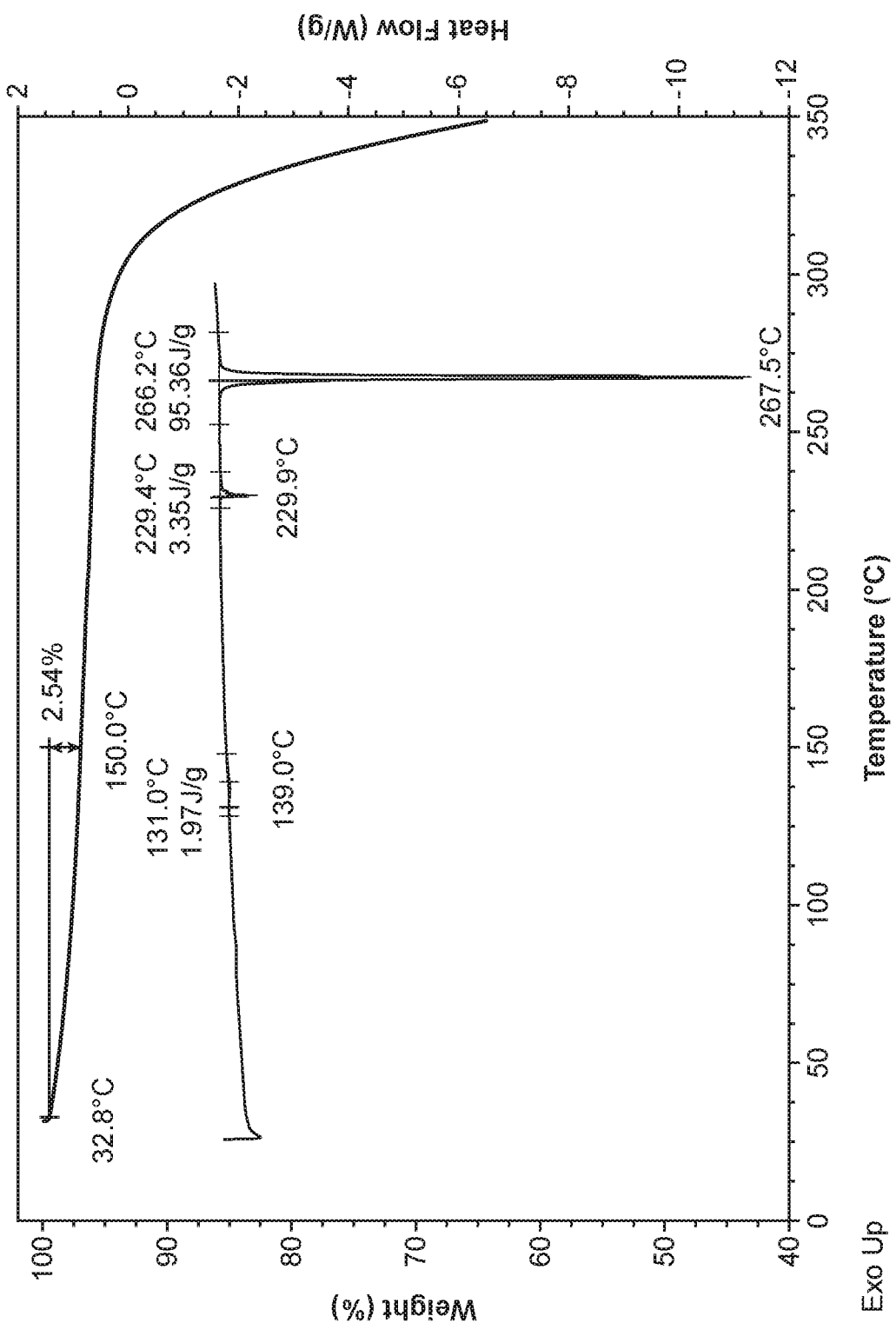
FIG. 13 is a thermogravimetric analysis (TGA) (top line) and a differential scanning calorimeter (DSC) curve (bottom line) of Compound I Form E.

Compound I Form E was generated via solution vapor diffusion in EtOAc/n-heptane at RT as discussed above. The XRPD pattern is displayed in FIG. 12 and TGA/DSC data are shown in FIG. 13. A weight loss of 2.5% was observed up to 150° C. and three endothermic peaks at 131.0° C., 229.4° C. and 266.2° C. (onset temperature) were observed by DSC. XRPD analysis indicated that Form E converted to Form A after heating to 150° C. $^1$H NMR (collected on Bruker 400M NMR Spectrometer using DMSO-d6) showed no solvent residue was detected. Thus, it is contemplated that Compound I Form E is an anhydrate or hydrate.

Example 4. Conversion Studies Among Forms of Compound I

Conversion Study Between Compound I Form a and Compound I Form C

The conversion relationship between anhydrous Compound I Form A and Compound I Form C was investigated via slurry turnover at various temperatures (RT (25±3° C.) or 50° C.) as follows.

About 5 mg of Compound I Form A was added to 1.0 mL of ACN, and the suspension was stirred at 50° C. for 2 hours to reach equilibrium. The suspension was filtered into a vial, which included 5 mg of Compound I Form A and Compound I Form C (mass ratio of 1:1). The mixture was stirred at a desired temperature for 4 days, and the solids were then analyzed by XRPD and DSC.

XRPD analyses showed that Form C converted to Form A at both RT and 50° C. In DSC, Form C was observed to convert to Form A after heating above the exothermic event. Thus, it is contemplated that the stability relationship between Form A and Form C is monotropic and Form A is more stable.

Conversion Study Between Compound I Form A and Compound I Form E

The conversion relationship between anhydrate Compound I Form A and Compound I Form E was investigated via slurry turnover at various temperatures (RT (25±3° C.) or 50° C.) and water activities as follows.

For various temperatures: About 5 mg of Compound I Form A was added to 1.0 mL of ACN, and the suspension was stirred at 50° C. for 2 hours to reach equilibrium. The suspension was filtered into a vial, which included 2 mg of Compound I Form A and Compound I Form E (mass ratio of 1:1). The mixture was stirred at a desired temperature for 4 days, and the solids were then analyzed by XRPD. These XRPD analyses showed that Form E converted to Form A at both RT and 50° C.

For various water activities: About 10 mg of Compound I Form A was added to 1.0 mL EtOH/H$_2$O with different a$_w$ (Table 12), and the suspension was stirred at RT for 1 hour to reach equilibrium. The suspension was filtered into a vial, which included 2 mg of Compound I Form A and Compound I Form E (mass ratio of 1:1). The mixture was stirred at the desired a$_w$ for 21 days, and the solids were then analyzed by XRPD.

TABLE 12

Slurry turnover between Form A and E at various water activities

| Starting Form | Aw (EtOH/H$_2$O, v/v) | Final Form |
|---|---|---|
| Form A + E | 0.298 (952:48) | Form A |
| | 0.605 (855:145) | Form A |
| | 0.900 (450:550) | Form A |

The XRPD analyses of these samples showed that Form E converted to Form A at different a$_w$ of 0.298, 0.605 and 0.900.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

What is claimed is:

1. A crystalline form of Compound I of Form B having the formula:

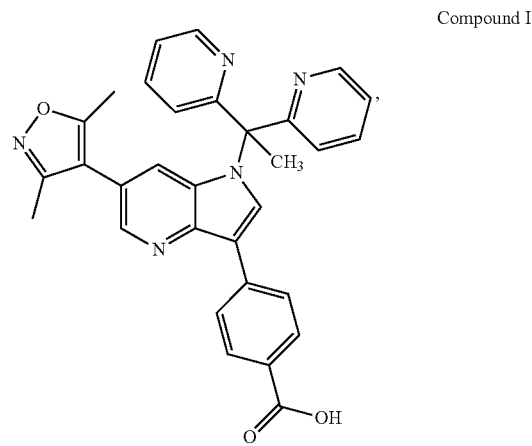 [SMILES: Cc1noc(C)c1-c1cnc2c(-c3ccc(C(=O)O)cc3)cn(C(C)(c3ccccn3)c3ccccn3)c2c1]

Compound I characterized by an X-ray powder diffractogram comprising the following peaks: 19.0, 21.0, and 24.8 °2θ±0.2 °2θ, as determined on a diffractometer using Cu-Kα radiation.

2. A method for treating a patient suffering from, or at risk of, a disease or condition mediated by a bromodomain, the method comprising administering to the patient in need thereof an effective amount of a crystalline form of claim 1, wherein the disease or condition is selected from the group consisting of: rheumatoid arthritis, osteoarthritis, ulcerative colitis, and atherosclerosis.

3. The crystalline form of claim 1, wherein the diffractogram further comprises one or more peaks at: 10.9, 17.2, or 18.0 °2θ±0.2 °2θ.

4. A crystalline form of Compound I of Form C having the formula:

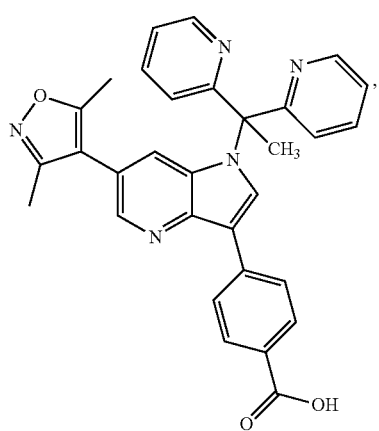

Compound I characterized by an X-ray powder diffractogram comprising the following peaks: 8.8, 17.1, and 17.7 °2θ±0.2 °2θ (Compound I Form C), as determined on a diffractometer using Cu-Kα radiation.

5. The crystalline form of claim 4, wherein the diffractogram further comprises one or more peaks at: 11.6 or 15.1 °2θ±0.2 °2θ.

6. A crystalline form of Compound I of Form D having the formula:

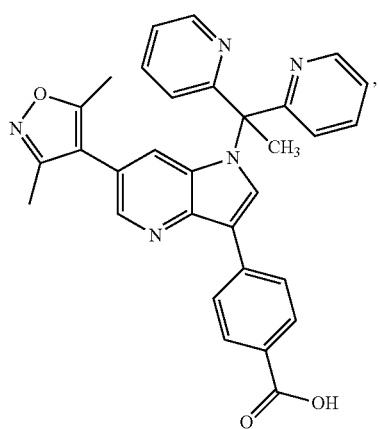

Compound I characterized by an X-ray powder diffractogram comprising the following peaks: 8.0, 16.1, and 20.2 °2θ±0.2 °2θ (Compound I Form D), as determined on a diffractometer using Cu-Kα radiation.

7. The crystalline form of claim 6, wherein the diffractogram further comprises one or more peaks at: 13.5 or 22.2 °2θ±0.2 °2θ.

8. A crystalline form of Compound I of Form E having the formula:

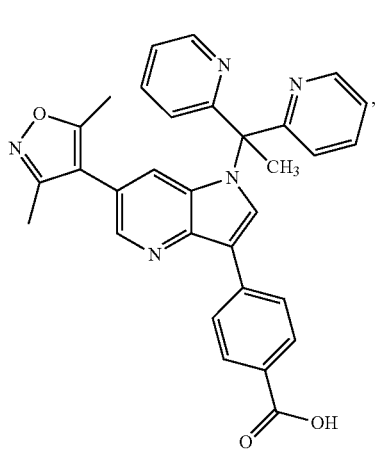

Compound I characterized by an X-ray powder diffractogram comprising the following peaks: 4.7, 9.4, and 18.8 °2θ±0.2 °2θ (Compound I Form E), as determined on a diffractometer using Cu-Kα radiation.

9. The crystalline form of claim 8, wherein the diffractogram further comprises one or more peaks at: 9.1, 14.1, or 18.2 °2θ±0.2 °2θ.

10. A pharmaceutical composition comprising a crystalline form of claim 1, and one or more pharmaceutically acceptable carriers.

11. A pharmaceutical composition comprising a crystalline form of claim 4, and one or more pharmaceutically acceptable carriers.

12. A pharmaceutical composition comprising a crystalline form of claim 6, and one or more pharmaceutically acceptable carriers.

13. A pharmaceutical composition comprising a crystalline form of claim 8, and one or more pharmaceutically acceptable carriers.

14. A method for treating a patient suffering from, or at risk of, a disease or condition mediated by a bromodomain, the method comprising administering to the patient in need thereof an effective amount of a crystalline form of claim 4, wherein the disease or condition is selected from the group consisting of: rheumatoid arthritis, osteoarthritis, ulcerative colitis, and atherosclerosis.

15. A method for treating a patient suffering from, or at risk of, a disease or condition mediated by a bromodomain, the method comprising administering to the patient in need thereof an effective amount of a crystalline form of claim 6, wherein the disease or condition is selected from the group consisting of: rheumatoid arthritis, osteoarthritis, ulcerative colitis, and atherosclerosis.

16. A method for treating a patient suffering from, or at risk of, a disease or condition mediated by a bromodomain, the method comprising administering to the patient in need thereof an effective amount of a crystalline form of claim 8, wherein the disease or condition is selected from the group consisting of: rheumatoid arthritis, osteoarthritis, ulcerative colitis, and atherosclerosis.

* * * * *